(12) United States Patent
Clarke et al.

(10) Patent No.: US 12,214,122 B2
(45) Date of Patent: Feb. 4, 2025

(54) DRY POWDER INHALER

(71) Applicant: VECTURA DELIVERY DEVICES LIMITED, Wiltshire (GB)

(72) Inventors: Roger Clarke, Cambridgeshire (GB); Andreas Meliniotis, Cambridgeshire (GB)

(73) Assignee: VECTURA DELIVERY DEVICES LIMITED (GB)

( * ) Notice: Subject to any disclaimer, the term of this patent is extended or adjusted under 35 U.S.C. 154(b) by 945 days.

(21) Appl. No.: 17/276,626

(22) PCT Filed: Sep. 16, 2019

(86) PCT No.: PCT/EP2019/074742
§ 371 (c)(1),
(2) Date: Mar. 16, 2021

(87) PCT Pub. No.: WO2020/058209
PCT Pub. Date: Mar. 26, 2020

(65) Prior Publication Data
US 2021/0268214 A1 Sep. 2, 2021

(30) Foreign Application Priority Data

Sep. 17, 2018 (EP) .................................... 18194962
Dec. 3, 2018 (EP) .................................... 18209763

(51) Int. Cl.
*A61M 15/00* (2006.01)
(52) U.S. Cl.
CPC .... *A61M 15/0051* (2014.02); *A61M 15/0025* (2014.02); *A61M 15/0026* (2014.02); *A61M 15/007* (2014.02); *A61M 2202/064* (2013.01)
(58) Field of Classification Search
CPC .............. A61M 15/00; A61M 15/0001; A61M 15/0003; A61M 15/0028; A61M 15/003;
(Continued)

(56) References Cited

U.S. PATENT DOCUMENTS

2004/0025877 A1* 2/2004 Crowder ........... A61M 15/0003
128/203.15
2005/0154491 A1* 7/2005 Anderson ............. A61M 15/00
700/236
(Continued)

FOREIGN PATENT DOCUMENTS

WO  WO 2005/037353 A1  4/2005
WO  WO 2009/092520 A1  7/2009
(Continued)

OTHER PUBLICATIONS

European Search Report from corresponding European Application No. 18194962.9, mailed Feb. 12, 2019.
(Continued)

*Primary Examiner* — Timothy A Stanis
*Assistant Examiner* — Nicholas B. Engel
(74) *Attorney, Agent, or Firm* — Davidson Kappel LLC

(57) ABSTRACT

The present invention provides an inhaler comprising a housing which contains a blister strip having a plurality of blisters which contain powdered medicament for inhalation, a mouthpiece mounted to the housing through which the medicament is inhaled by a user, an indexing and opening mechanism for indexing the blister strip and for opening the blisters which is operated by an actuator, wherein the blister strip is indexed by forward motion of the actuator from a first position to a second position, such as by opening a cover, and is also indexed in the same direction by reverse motion of the actuator from the second positon to the first position, such as by closing the cover.

15 Claims, 27 Drawing Sheets

(58) Field of Classification Search
CPC .......... A61M 15/0035; A61M 15/0038; A61M 15/004; A61M 15/0041; A61M 15/0045; A61M 15/0046; A61M 15/0051; A61M 15/0055; A61M 15/0056; A61M 2202/064
See application file for complete search history.

(56) References Cited

U.S. PATENT DOCUMENTS

| | | | | |
|---|---|---|---|---|
| 2005/0268909 | A1* | 12/2005 | Bonney | A61M 15/0043 |
| | | | | 128/203.15 |
| 2006/0196504 | A1* | 9/2006 | Augustyn | A61M 15/0045 |
| | | | | 128/203.15 |
| 2007/0062525 | A1* | 3/2007 | Bonney | A61M 15/0051 |
| | | | | 128/203.15 |
| 2007/0267016 | A1* | 11/2007 | Thoemmes | A61M 15/0045 |
| | | | | 128/203.15 |
| 2008/0308102 | A1* | 12/2008 | Davies | A61M 15/0086 |
| | | | | 128/203.15 |
| 2011/0226244 | A1* | 9/2011 | Perkins | A61M 15/0045 |
| | | | | 128/203.15 |
| 2016/0193433 | A1* | 7/2016 | Thoemmes | A61M 15/0035 |
| | | | | 128/203.15 |

FOREIGN PATENT DOCUMENTS

| | | |
|---|---|---|
| WO | WO 2012/069854 A2 | 5/2012 |
| WO | WO 2013/175176 A1 | 11/2013 |
| WO | WO 2013/175177 A1 | 11/2013 |

OTHER PUBLICATIONS

International Search Report from corresponding International Application No. PCT/EP2019/074742, mailed Nov. 27, 2019.
Written Opinion of the International Searching Authority issued on Nov. 27, 2019, from corresponding International Application No. PCT/EP2019/074742.

* cited by examiner

DRY POWDER INHALER

This application is a U.S. national phase application under 35 U.S.C. of § 371 of International Application No. PCT/EP2019/074742, Sep. 16, 2019, which claims priority of European Patent Application No. EP 18194962.9, filed Sep. 17, 2018, and European Patent Application No. EP 18209763.4, filed Dec. 3, 2018, the disclosures of which are hereby incorporated by reference herein.

TECHNICAL FIELD OF THE INVENTION

The present invention relates to a dry powder inhaler with a blister strip containing doses of one or more substances for inhalation.

BACKGROUND TO THE INVENTION

Inhalers provide an attractive method for administering medicaments, for example to treat local diseases of the airway or to deliver drugs to the bloodstream via the lungs. The medicament is commonly provided as a dry powder pre-packaged in individual doses, such as capsules or blisters. It is advantageous for the inhaler to hold a number of doses so that there is no need to insert a blister into the device each time it is used. Therefore, many inhalers include means for storing a number of doses, e.g. in the form of a blister strip. Such devices are disclosed in, for example, WO 05/037353, WO 12/069854 and WO13/175176.

In the treatment of respiratory disorders it is often beneficial to administer a combination of active pharmaceutical ingredients (APIs) to a patient, for example a bronchodilator and an anti-inflammatory drug, such as salmeterol and fluticasone, or a triple combination such as a long acting β2-agonist (LABA), a long-acting muscarinic antagonist (LAMA) and a corticosteroid. However, the APIs typically have very different physicochemical properties; this affects, for example, their interactions with carrier particles. Consequently, it is very difficult to co-formulate two or three APIs in a single powder with the desired aerosolization properties.

One way to circumvent this problem is separate the APIs. For example, WO 00/064519 discloses a bulk powder device with separate reservoirs for each API. On actuation of the device, a dose of each formulation is dispensed, which is aerosolized as the patient inhales. WO 05/014089 discloses a device which has two separate blister strips, each containing an independent drug blend. The strips are indexed and opened concurrently when the device is actuated, so that the patient receives both APIs on inhalation. However, these devices are necessarily more complex than devices which dispense a single formulation.

WO 09/092520 discloses inhalers which can deliver different inhalation formulations during each use. In an indexing operation, a mouthpiece cover is pivoted from a closed to an open position by the user. The first phase of the cover opening causes an actuator to withdraw the piercer from the previously opened and emptied blister pocket. The second phase of the cover opening causes an indexing wheel to move the blister strip onward to the next blister pocket. Once the cover has been fully opened, the user pivots the actuator back to the closed position, in order to pierce the newly aligned blister pocket. Finally, after inhalation, the user pivots the cover back to the closed position. The indexing wheel is disengaged from the cover in the closing step, so that the blister strip is not moved backwards. In one embodiment, the inhaler is adapted to move the blister strip onwards by two blister pockets in each indexing operation, and has two piercing elements for simultaneously piercing the blister pockets aligned with each piercing element. However, indexing forward by two blisters on opening the cover either requires that the angle through which the cover pivots is increased, or that the gear ratio between the cover and the indexing wheel is changed, so that the same pivot angle moves the blister strip twice as far. Typically the cover is pivoted through approximately 90° on opening/closing, which is sufficient to expose the mouthpiece. However, increasing this to approximately 180° would make the device less easy to use. Effectively only one edge of the device is always exposed, which severely restricts where the user can hold the main body of the device in one hand while opening the outer cover with the other. On the other hand, significantly increasing the torque required to pivot the cover also makes the inhaler harder to operate, especially for elderly patients. Hence, a need exists for improved devices which overcome these issues.

BRIEF DESCRIPTION OF THE INVENTION

The present invention addresses these problems, and in a first aspect, it provides an inhaler comprising a housing which contains a blister strip having a plurality of blisters which contain powdered medicament for inhalation, a mouthpiece mounted to the housing through which the medicament is inhaled by a user, an indexing and opening mechanism for indexing the blister strip and for opening the blisters which is operated by an actuator, wherein the blister strip is indexed by forward motion of the actuator from a first position to a second position, characterized in that the blister strip is also indexed in the same direction by reverse motion of the actuator from the second positon to the first position.

The inhaler of the invention allows the contents of two or more blisters to be dispensed on each actuation, for example from a blister strip that contains two or more different formulations. When the user inhales through the mouthpiece, an airflow is generated through the opened blisters to entrain the medicament and carry it via the mouthpiece, into the user's airway. It also allows the effort that is required for indexing and piercing to be distributed over both the forward and reverse motions (such as opening and closing a cover), so that the torque that must be applied by the user to operate the device is reduced.

Preferably the indexing and opening mechanism is arranged to index the blister strip forwards by one blister on each of the forward and reverse motions of the actuator and to open two blisters. Thus, on inhalation, the user receives the contents of two blisters. More preferably the two blisters contain different medicaments.

Preferably the inhaler has an outer cover which is pivotally mounted on the housing.

In one embodiment, the outer cover forms the actuator so that motion of the outer cover causes indexing of the blister strip and opening of the blisters. Preferably in the first position the outer cover is closed so that the mouthpiece is covered, and in the second position the outer cover is open so that the mouthpiece is exposed.

In an alternative embodiment, the inhaler has a lever which forms the actuator so that motion of the lever causes indexing of the blister strip and opening of the blisters.

Preferably, the opening mechanism comprises a piercer and the indexing mechanism indexes one or more blisters into alignment with the piercer for piercing. More preferably, the blister strip is indexed during a first part of the forward motion of the actuator, the piercer pierces one or more aligned blisters during a second part of the forward motion, the piercer is removed from the blister(s) during a first part of the reverse motion of the actuator and the blister strip is indexed again during a second part of the reverse motion.

In one embodiment, the indexing and opening mechanism comprises first and second drive gears, an idler gear and a blister strip indexing wheel, wherein the actuator is drivingly linked to the first drive gear, and to the second drive gear via the idler gear so that the first and second drive gears rotate in opposite senses during motion of the actuator; wherein the first drive gear drives the indexing wheel during at least part of the forward motion of the actuator, and does not drive the indexing wheel during the reverse motion of the actuator; and the second drive gear drives the indexing wheel during at least part of the reverse motion of the actuator, and does not drive the indexing wheel during the forward motion of the actuator. The term "drivingly linked" includes both direct engagement and indirect linkage that transmits drive, such as via one or more intermediate gears.

Preferably, the indexing and opening mechanism comprises first and second actuator gears which are connected to and driven by the actuator, wherein the first actuator gear drives the first drive gear, and the second actuator gear drives the idler gear which in turn drives the second drive gear.

Preferably, the first and second drive gears are axially linked together to form a shuttle whilst being free to rotate independently, wherein the first and/or second drive gear has a track follower which interacts with a track formation on the housing to cause the shuttle to translate axially relative to the indexing wheel so that the first and second drive gears engage and disengage with the indexing wheel. More preferably, the first and second drive gears each have a ramp follower which interacts with ramps on the housing to cause the first and second drive gears to disengage with the indexing wheel in the first and second positions, and preferably also during piercing and removal of the piercer.

Alternatively, a first drive coupling is connected to the first drive gear, a second drive coupling is connected to the second drive gear, and the drive couplings engage and disengage with the indexing wheel.

In another embodiment, the indexing and opening mechanism comprises first and second drive gears that are connected to a blister strip indexing wheel, and an idler gear, wherein the actuator is drivingly linked to the first drive gear during at least part of the forward motion of the actuator, and is not drivingly linked to the first drive gear during the reverse motion of the actuator; and the actuator is drivingly linked to the idler gear and the second drive gear during at least part of the reverse motion of the actuator, and is not drivingly linked to the second drive gear during the forward motion of the actuator. Preferably, a dual drive coupling is connected to and driven by the actuator, and the dual drive coupling goes into and out of driving linkage with the first and second drive gears.

Preferably, the indexing and opening mechanism comprises a first actuator gear which drives the first drive gear and a second actuator gear which drives the idler gear which in turn drives the second drive gear so that the first and second actuator gears rotate in opposite senses during motion of the actuator, and the dual drive coupling engages and disengages with the first and second actuator gears.

In a specific embodiment, the present invention provides an inhaler comprising a housing which contains a blister strip having a plurality of blisters which contain powdered medicament for inhalation, a mouthpiece mounted to the housing through which the medicament is inhaled by a user, an outer cover which is mounted on the housing so that it pivots between a first, closed position in which the outer cover covers the mouthpiece, and a second, open position in which the mouthpiece is exposed, and an indexing and piercing mechanism; wherein pivoting the outer cover from the closed position to the open position causes the blister strip to be indexed by one blister and causes two blisters to be pierced, and wherein pivoting the outer cover from the open position to the closed position also causes the blister strip to be indexed by one blister in the same direction.

BRIEF DESCRIPTION OF THE FIGURES

The invention will now be further described with reference to the Figures, wherein.

DETAILED DESCRIPTION OF THE INVENTION

Figure 1A:
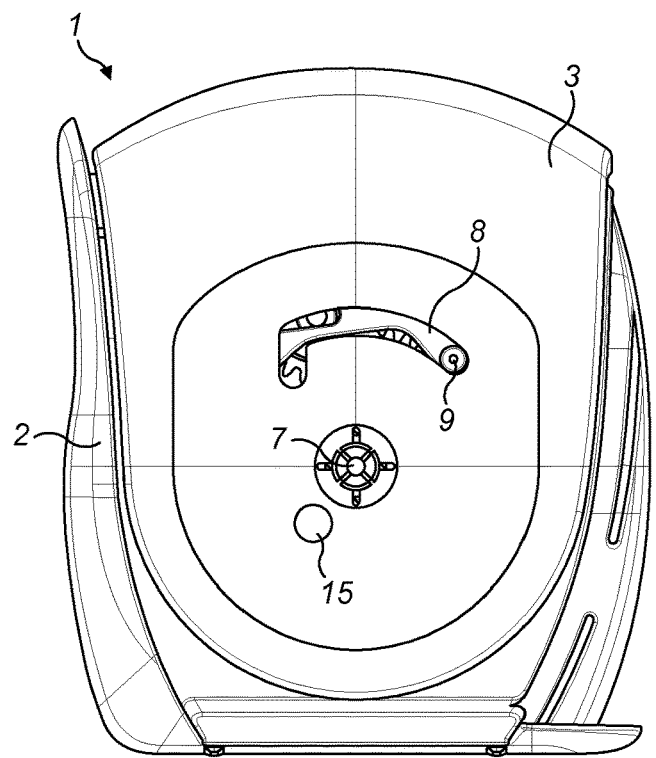
FIGS. 1A and 1B show an inhaler of the invention with the outer cover in the closed and opened positions respectively.
Figure 1B:
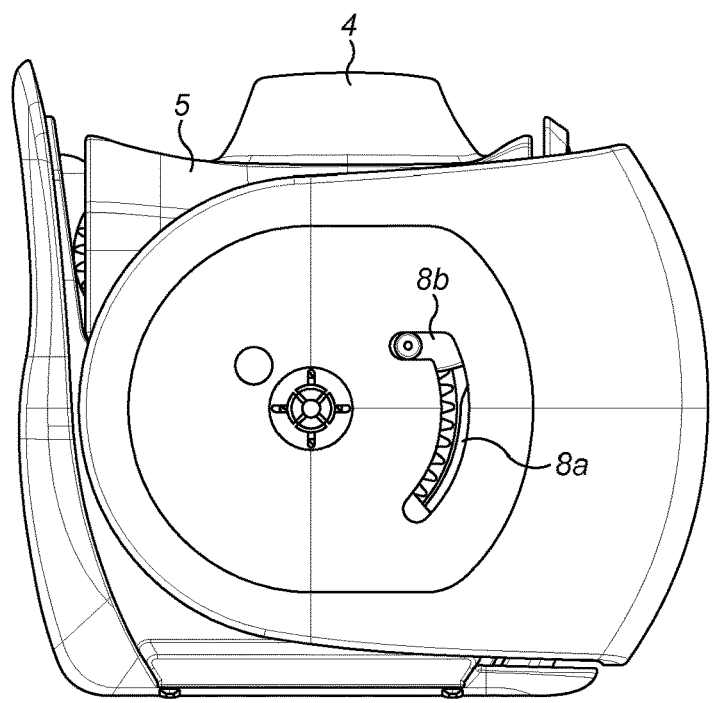

FIG. 1 shows an inhaler according to the invention. The inhaler 1 has a housing 2 formed from two shell portions 2a, 2b and an outer cover (or cap) 3. The outer cover is pivotally mounted to the housing. The outer cover 3 can be rotated through approximately 90° from a closed position as shown in FIG. 1A in which the outer cover 3 covers and protects a mouthpiece 4 to a fully open position, shown in FIG. 1B in which the mouthpiece 4 is exposed to enable a user to inhale a dose of medicament.

Figure 1C:
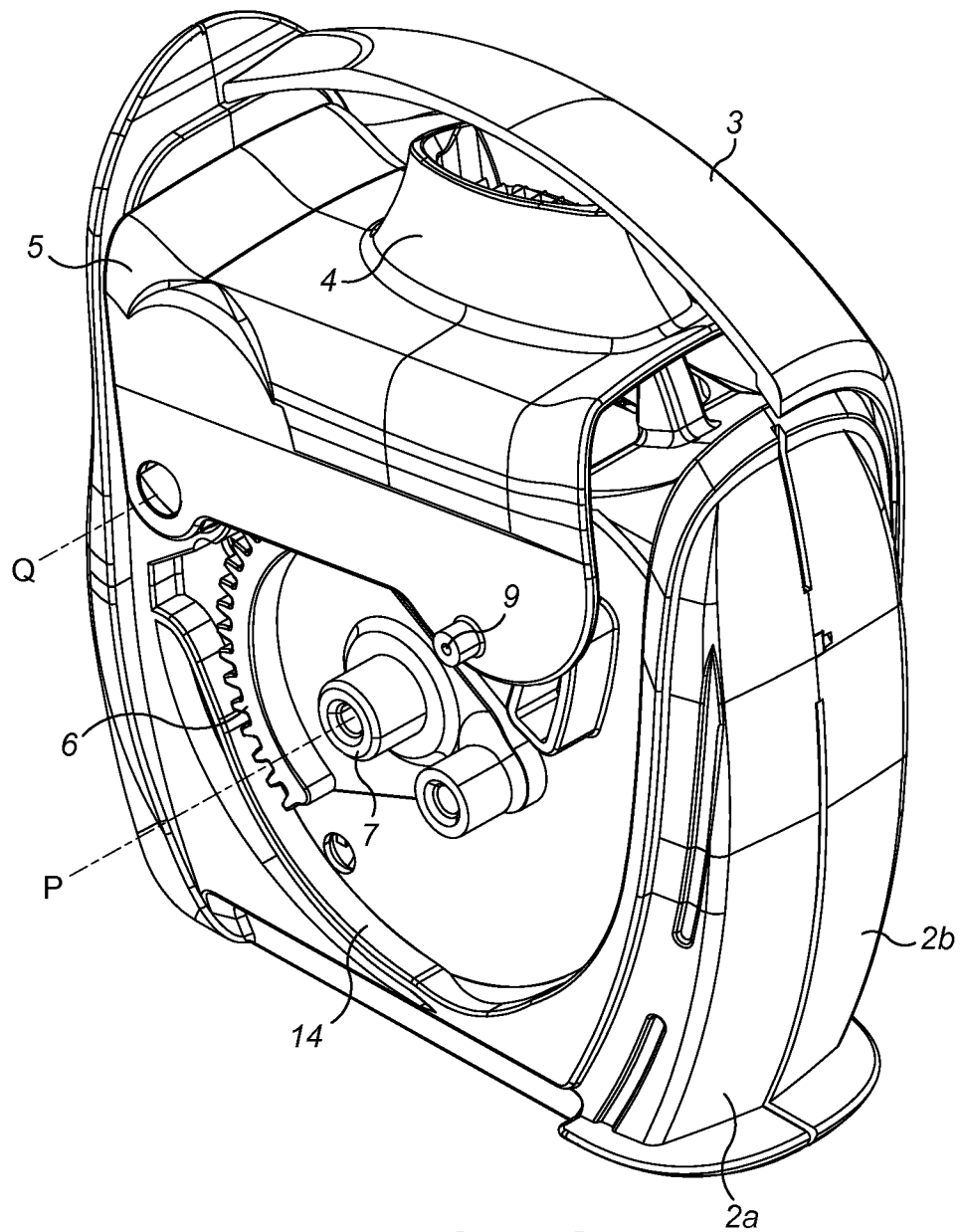
FIG. 1C shows the inhaler with one side of the outer cover removed so that the internal components are visible.

FIG. 1C shows the inhaler with the outer cover 3 partially cut away so that some of the internal components can be seen. The outer cover is mounted for rotation on axles 7 located on axis P on either side of the housing. The mouthpiece 4 is attached to or formed as part of a mouthpiece support member 5 which is pivotally mounted to the housing about a second axis Q. A piercer (not visible in FIG. 1) is located on the underside of the support member 5 directly beneath the mouthpiece 4. A cam 9 is located on one side of the mouthpiece support member 5 and cooperates with a cam slot 8 in the outer cover 3 to cause the mouthpiece support member and the piercer to pivot in a manner which is described below. Alternatively, the mouthpiece support member could be fixed to the housing, and the piercer may be pivotally mounted to the mouthpiece support member so that the piercer pivots relative to the mouthpiece.

The inhaler has an indexing mechanism 6 (only part of which is visible) that selectively couples the outer cover to a blister strip indexing wheel. The outer cover is connected to the indexing mechanism in a manner which is explained below. Pivoting the outer cover between the closed and open positions causes the indexing wheel to index (i.e. sequentially move) the blister strip and also causes the piercer to pierce one or more blisters. The user then inhales through the mouthpiece, which aerosolizes the powder in the pierced blister(s).

The inhaler of the invention differs from previous inhalers (such as those described in WO13/175177) in that the blister strip is moved forwards by both opening and closing the outer cover. This makes it possible, for example, to index and pierce a pair of blisters on each complete actuation (i.e. a full opening and closing cycle) of the device, so that the user inhales the contents of both blisters simultaneously.

FIG. 2 schematically shows a blister strip 11 suitable for use in the inhaler of the invention, having blisters 12 containing two different formulations. The blister strip is typically cold formed from a ductile foil laminate or a plastics material and includes a pierceable lid, typically foil or a foil laminate, which is heat-sealed around the periphery of the blister after the dose of medicament has been introduced during manufacture.

The blisters 12 are arranged in pairs, in which one blister of each pair contains a first formulation (A) and the other contains a second formulation (B) in alternating sequence (ABAB). Typically the two formulations contain different APIs, although the formulations could also contain, for example, a single API with two different particle sizes and/or mixed with different excipients and/or prepared by different processes.

The inhaler is configured to operate with this blister strip so that it indexes and opens two blisters on each complete actuation in a manner which will be explained below, so that the user inhales the contents of both blisters simultaneously.

As shown schematically in FIG. 2, the piercer 10 has two piercing elements 10a, 10b which face the blister strip 11, one piercing element for each of the two blisters that are pierced in a single actuation. The piercing elements may be identical, but may also be different, for example if it is desired to create openings of different sizes in the two blisters, due to the different properties of the two formulations.

Each piercing element has a pair of piercing teeth, for creating two openings in the lid of each blister so that air is drawn into the blister through one opening and flows out of the blister together with an entrained dose of medicament through the other opening and via the mouthpiece into the user's airway. Alternatively, the piercing element may have a larger number of teeth for creating two or more inlet openings and/or two or more outlet openings; or the piercing element could create a single large opening which allows air to flow both into and out of the blister. The piercer is preferably formed as a single component.

The ABAB blister configuration has the advantage that each piercing element, and the associated airway to the mouthpiece, always interacts with the same formulation (i.e. either A or B, but never A in one actuation and then B in the next). Therefore the piercer and airway can be designed or customised to be optimal for that particular formulation.

Alternatively, an ABBA arrangement is possible, with an AB pair being followed on the next use by a BA pair. In each case, the user receives one blister of formulation A and one blister of formulation B (provided of course that the blister strip is correctly positioned initially). This configuration has the advantage that it may be simpler to manufacture, because the number of pairs of adjacent blisters which contain different formulations is halved.

The blister strip preferably has numbers printed on it that are visible to the user, for example through a window in the housing, in order to display the number of remaining (or used) doses. This is preferable to having a separate dose counter, because there is no possibility of the incorrect dose number being displayed. In a device which has two blister strips, either or both of the strips could be numbered. However, if one of the strips is not indexed correctly for any reason, then dose count could be incorrect or misleading. If only one strip is numbered, then the displayed number would be incorrect for one of the formulations, but the user would have no way of knowing this. If both strips are numbered then the displayed numbers would differ and the user would be unable to tell which is correct. Thus, an advantage of an advantage of having both formulations in a single blister strip is that the displayed number is always correct.

In a further configuration, each blister could contain the same formulation, so that the inhaler provides a double dose. Another possibility is for each blister to contain a half dose, so that opening two blisters provides a single dose. This has the advantage that variations in the amount of powder dispensed into each blister result in smaller variations in the total amount of powder dispensed on actuation. This is because, on average, too large an amount in one blister may be compensated by too small an amount in the other, leading to a reduction in the variability of the total amount of powder dispensed.

Although the inhaler of the invention is particularly suitable for indexing and piercing two blisters in each actuation, it can also be arranged to index and piece other numbers of blisters. For example, the inhaler may have a single piercing element and is correspondingly arranged to index the blister strip by one blister pitch on each complete actuation, i.e. to move the strip by half of the blister pitch on each of the opening and closing strokes. The inhaler can therefore operate in a conventional manner (one blister per operation). However, the angular motion of the outer cover that is available for indexing is doubled. The torque required to index the blister is reduced because the work is spread over two operations (opening and closing). The inhaler is therefore suitable for the elderly, infirm or other users who may find it difficult to operate a conventional inhaler, such as young children. Alternatively, the additional angular motion could be used for other purposes. For example, the force applied during piercing could be increased, so that, for example, blisters with tougher and/or thicker lids could be used, or larger openings could be created, or the piercer could pierce through both the lid and the base of each blister. Other possibilities include increasing the amount of force for crushing the used blisters, which would reduce the size of the used blister strip; or compressing a spring which, when released, could apply an impulse to the next unused blister and thereby help to de-agglomerate the powder.

Similarly, the inhaler may have three piercing elements and the indexing mechanism may be correspondingly arranged to move the blister strip by one and a half blister pitches on each of opening and closing. Thus the inhaler can deliver three different formulations in a single operation from a blister strip having an ABCABC pattern, or a double dose of one formulation and a single dose of another from a blister strip having an AABAAB pattern. Likewise, it could deliver a triple dose of a single formulation. Furthermore, it is possible to use a blister strip containing four different formulations by indexing two blisters on each of opening and closing, and piercing four blisters. Whilst this could in principle also be achieved in an analogous manner to WO 09/092520 (i.e. indexing and piercing three or four blisters in a single actuating stroke), the torque required to do so would be very large, which could make the inhaler impractical. In contrast, spreading the work across the opening and closing strokes reduces the required torque to a manageable level. Other numbers and combinations of blisters are also possible, and those skilled in the art will be able to adapt the blister strip and inhaler accordingly.

The sequence of steps during indexing and piercing is schematically shown in FIG. 2. Only six blisters are shown for illustration, but typically the strip actually has 30 or 60 blisters.

Indexing takes place during the first part of the opening movement (or "stroke"), e.g. as the outer cover is pivoted from 0 to 60°. Piercing occurs during the remainder of the opening movement, e.g. as the outer cover is pivoted from 60 to 90°, while the blister strip is stationary. The blister strip is indexed from left to right. The first two unused blisters 12a, 12b are the next ones to be pierced. To the left of these are further unused blisters 12c, and to the right are used blisters 12d which have already been pierced and whose contents have been inhaled.

Figure 2A:
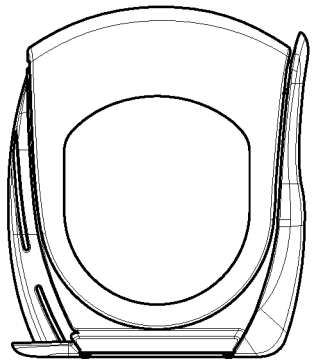
FIG. 2 shows the sequence of steps during operation of an inhaler according to the invention.
Figure 2A:
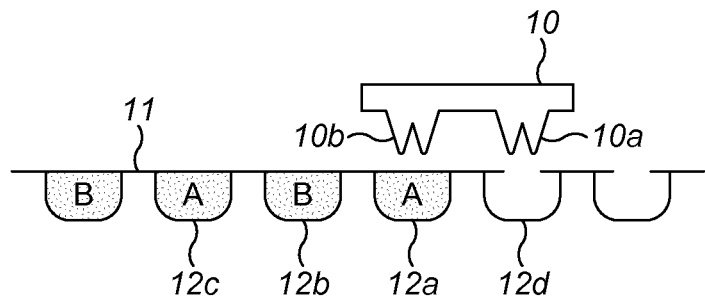

FIG. 2A shows the configuration when the outer cover is closed. The leading unused blister 12a is aligned with piercing element 10b. The second unused blister 12b has not yet been brought into alignment with the piercer. A used blister 12d is aligned with the other piercing element 10a.

Figure 2B:
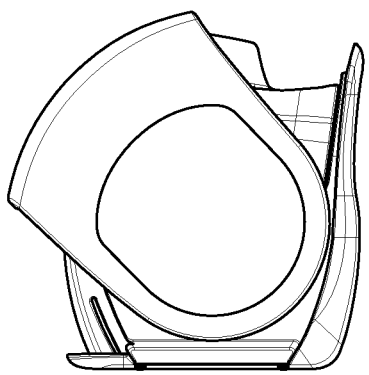
Figure 2B:
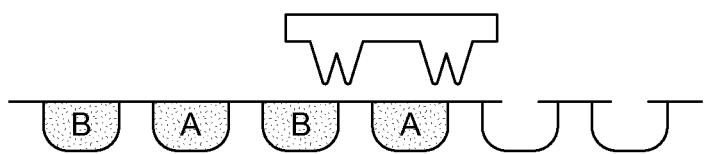

As the user begins to rotate the outer cover, the blister strip indexed forwards. FIG. 2B shows the outer cover part way through the first part of the opening movement, with the blister strip having moved forwards by about two thirds of the blister pitch.

Figure 2C:
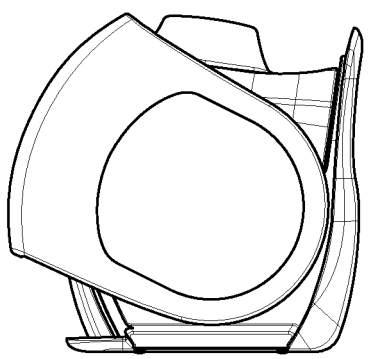
Figure 2C:
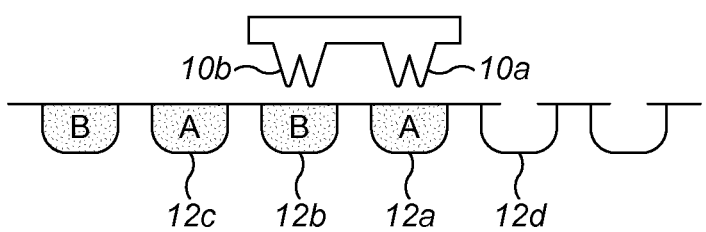

FIG. 2C shows the configuration at the end of the first part of the opening movement. The blister strip has indexed forward by one blister, so that the first two unused blisters 12a, 12b are aligned with the two piercing elements 10a, 10b. Up to this point, the actuation of the inhaler is reversible, because piercing has not yet occurred. The user can abort by simply closing the outer cover, which moves the blister strip back to the position of FIG. 2A.

Figure 2D:
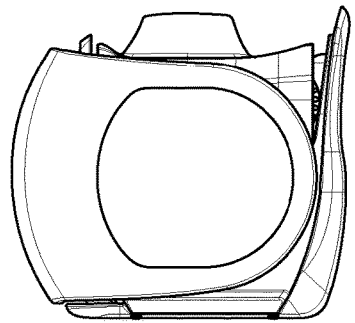
Figure 2D:
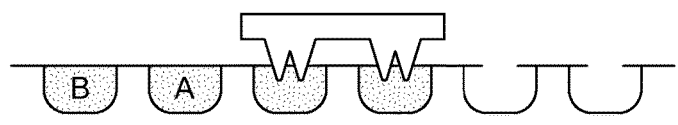

When the outer cover is rotated beyond this point through the second part of the opening stroke, the indexing mechanism is disengaged, and the piercer begins to pivot so that the piercing elements 10a, 10b pierce the two aligned and now stationary blisters 12a, 12b. FIG. 2D shows the fully open position, in which the blisters have been pierced. The user then inhales through the mouthpiece, which aerosolizes the powder in the pierced blister.

Figure 2E:
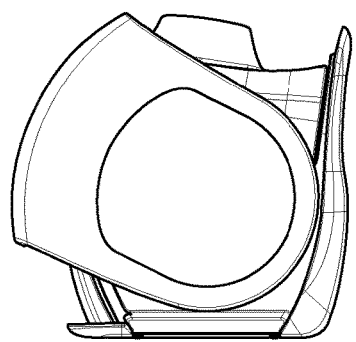
Figure 2E:
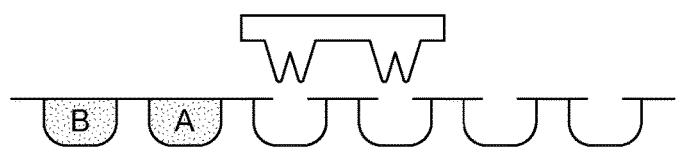

As the outer cover is closed, the piercing elements are withdrawn from the pierced blisters in the first part of the closing stroke, e.g. as the outer cover is pivoted from 90 to 60° while the blister strip remains stationary, shown in FIG. 2E.

Figure 2F:
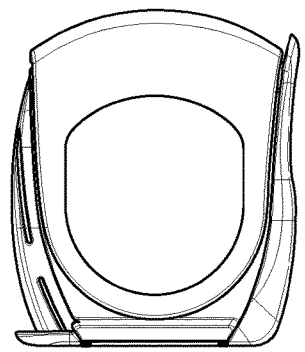
Figure 2F:
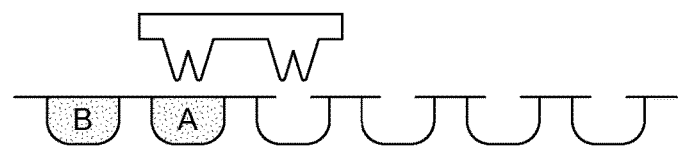

Up to this point, the operation of the inhaler is similar to that of WO 13/175177, except that it has two piercing elements instead of one. However, in the inhaler of WO 13/175177, the blister strip remains stationary during the second part of the closing stroke. In contrast, the inhaler of the invention also indexes the blister strip during the second part of the closing stroke, e.g. as the outer cover is pivoted from 60 to 0°. This is achieved by using a different indexing mechanism. Thus, as shown in FIG. 2F, at the end of the closing stroke, the blister strip has been indexed forwards by a further blister. Consequently, the inhaler has indexed and pierced two blisters in one complete actuation. In FIG. 2F, the inhaler is in the same state as in FIG. 2A, except that two further blisters have been emptied.

Figure 3A:
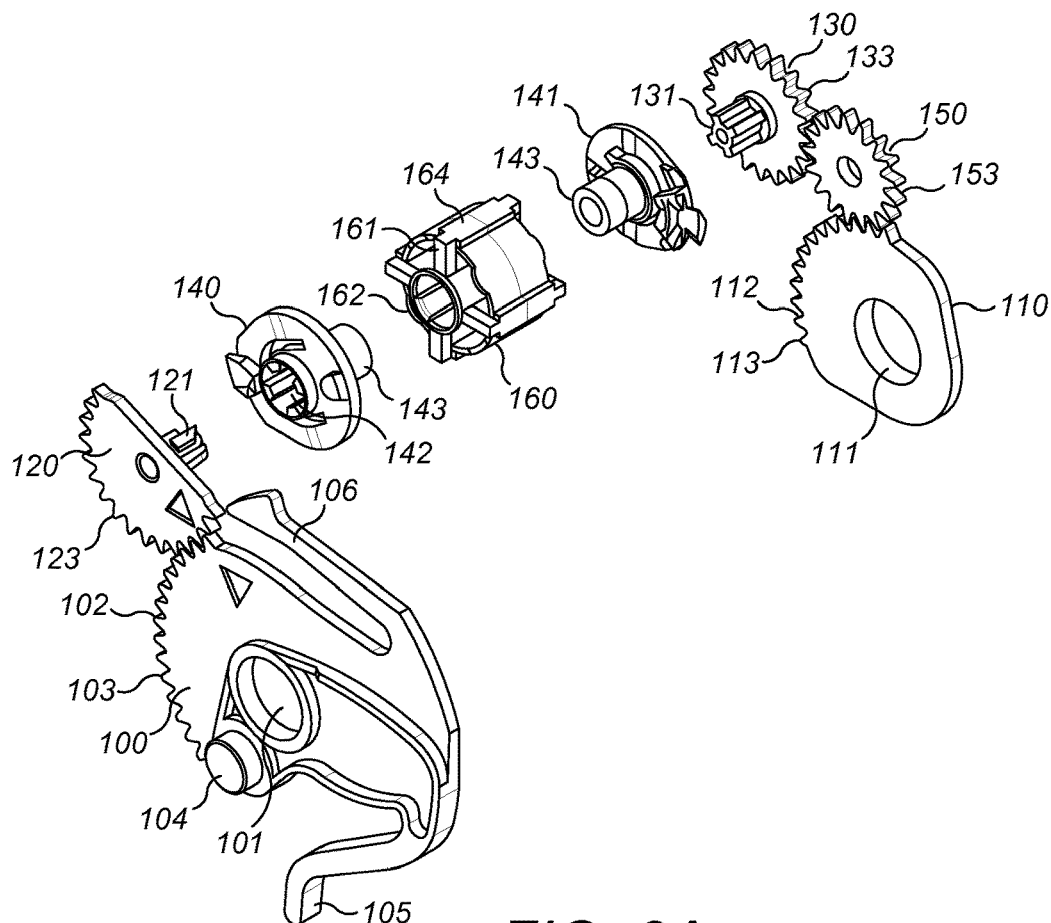
FIGS. 3A and 3B show expanded and assembled views of the indexing mechanism of a first embodiment of an inhaler according to the invention.
Figure 3B:
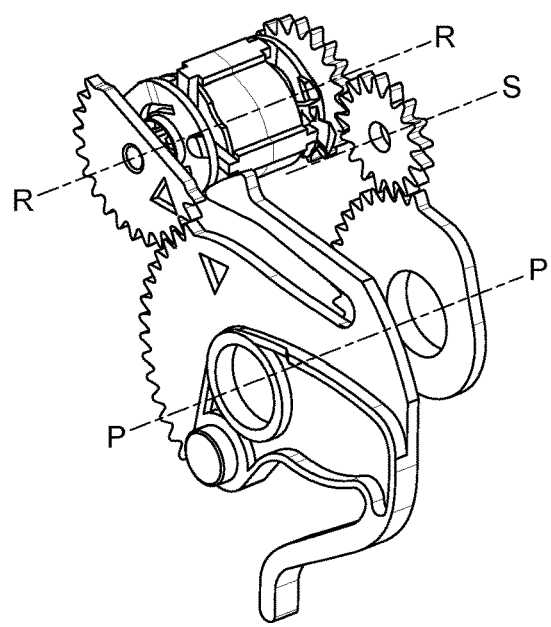

FIGS. 3A and 3B show expanded and assembled views of the indexing mechanism of a first embodiment of an inhaler according to the invention. The left hand side of the mechanism is similar to that of WO 13/175177, comprising a first (opening) actuator gear 100, a first drive gear 120, a first drive coupling 140 and a blister strip indexing wheel 160. However, unlike WO 13/175177, the mechanism additionally comprises a second (closing) drive coupling 141, a second drive gear 130 and an idler gear wheel 150 which connects the second drive gear to a second actuator gear 110.

The first and second actuator gears 100, 110 are formed as plate-like portions, each having a central pivot hole 101, 111 which fits onto the axles 7 (see FIG. 1C) on either side of the housing, so that the actuator gears are mounted for rotation about the same axis P as the outer cover. The actuator gears 100, 110 each have gear elements 102, 112 which consist of teeth 103, 113 extending around about a quarter of the periphery.

The first and second actuator gears 100, 110 may be keyed or otherwise attached to the outer cover when the inhaler is assembled so that the first and second actuator gears and the outer cover rotate together. For example, a round post 104 protrudes from each actuator gear and is received in a corresponding hole 15 in the outer cover 3 (shown in FIG. 1A). Opening or closing the outer cover thereby causes the actuator gears 100, 110 to rotate about axis P. Alternatively, the first and second actuator gears 100, 110 and outer cover may be formed as a single component, for example they may be moulded together as a unitary piece.

The first and second drive gears 120, 130 are mounted for rotation about a third axis R by means of shafts 121, 131.

The first actuator gear element 102 transmits drive from the outer cover as it is rotated to the first drive gear 120 by means of the gear teeth 103 which mesh with corresponding gear teeth 123 on the first drive gear 120.

The second actuator gear element 112 transmits drive from the outer cover as it is rotated via the idler gear wheel 150 to the second drive gear 130. The idler gear wheel is mounted for rotation about a fourth axis, S on an idler gear axle on the housing. The gear teeth 113 of the actuator gear element mesh with the gear teeth 153 on the idler gear wheel which in turn mesh with the gear teeth 133 on the second drive gear 130.

Thus the first drive gear 120 rotates in response to rotation of the first actuator gear 100, and the second drive gear 130 rotates in response to rotation of the second actuator gear 110, but in the opposite sense, due to the presence of the idler gear wheel 150.

Each drive gear 120, 130 is fixedly attached to its respective drive coupling 140, 141 by its shaft 121, 131. The shafts are cruciform in cross-section and fit into corresponding recesses 142 in the shafts 143 of the drive couplings (only the recess in the first drive coupling is visible in FIG. 3A). Thus the drive couplings 140, 141 rotate together with their respective drive gear 120, 130 in response to rotation of the actuator gears 100, 110 at all times.

The indexing wheel 160 comprises a number of spokes 161 (typically four) extending from a hub 162. The spokes are arranged so that a blister locates between the protruding ends 164 of successive spokes as the blister strip passes around the indexing wheel.

The manner in which the drive couplings 140, 141 selectively connect to and disconnect from the indexing wheel is described in detail in WO13/175177. Briefly, the drive couplings operate as follows. The shaft 143 of each drive coupling fits into a recess inside the hub 162 of the indexing wheel and provide bearing surfaces on which the indexing wheel 160 rotates. The indexing wheel is therefore coaxial with the drive gears 120, 130 on axis R. The drive couplings 140, 141 selectively connect and disconnect the drive gears 120, 130 to the indexing wheel 160, so that, when coupled, the indexing wheel 160 rotates in response to rotation of the outer cover to index the blister strip.

Figure 4A:
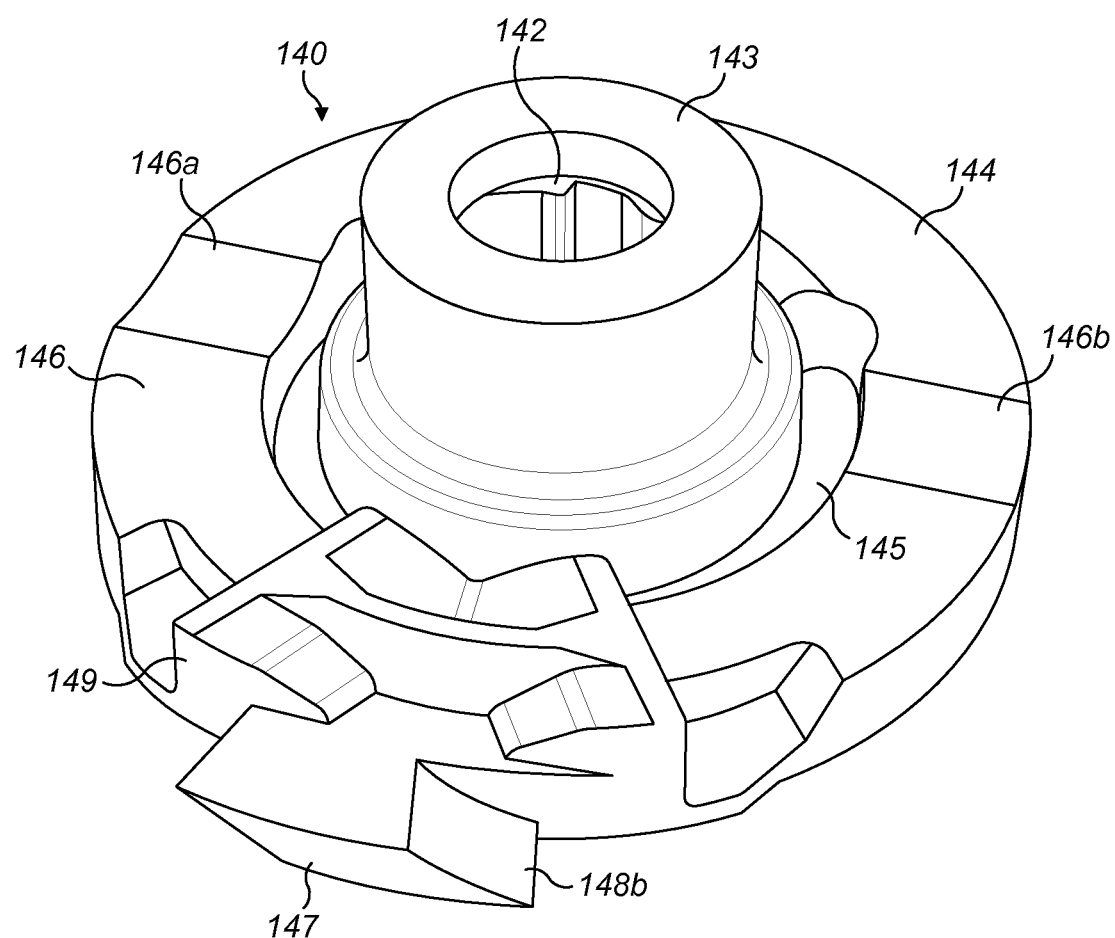
FIGS. 4A and 4B show perspective and side views of the drive coupling of the first embodiment.
Figure 4B:
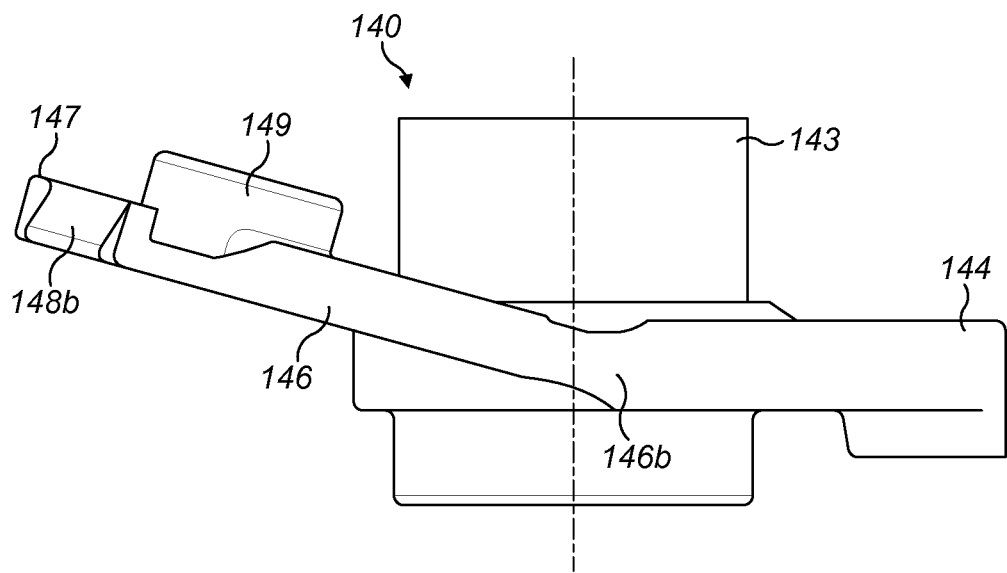

FIGS. 4A and 4B show perspective and side views of a drive coupling 140. Each drive coupling has a circular flange 144 that extends radially from one end of the shaft 143. The flange 144 has a cut-away arcuate opening 145 where the flange 144 joins the shaft 143 so that approximately half 146 of the flange is not directly attached to the shaft 143 but only to the remaining portion of the flange 144 at each of its ends 146a, 146b. As a result, this portion 146 of the flange 144 is flexible and can be deflected out of the plane of the flange 144 towards or away from the indexing wheel when force is applied to it. The flange 144 is made from a resilient material so that when the deflected flexible flange portion 146 is released, it returns to its neutral position, in which it is coplanar with the remaining fixed portion of the flange 144. The flexible flange portion 146 has an integrally formed flange deflecting dog 147 projecting radially from its outer edge. The flange deflecting dog 147 has first and second angled engaging faces 148a, 148b on opposite sides, only one of which is visible in FIG. 4.

Figure 4C:
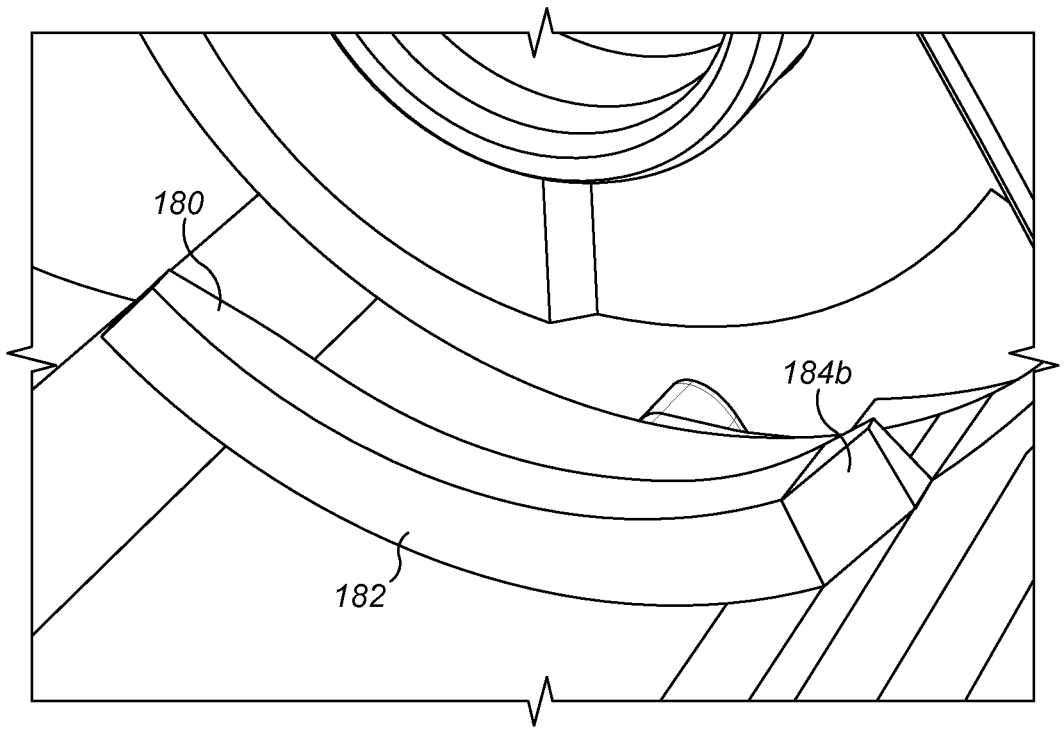
FIG. 4C shows the track formation

On the inside of each shell portion 2a, 2b of the housing 2 there is a track formation 180, one for each of the drive couplings. As shown in FIG. 4C, the track formation 180 is in the form of a barrier which separates and defines tracks 182 on either side. Each end of the barrier has an angled face 184a,b (only the track and angled engaging face on the outer side are visible in FIG. 4C).

When the drive gear is rotated in a first direction, the first drive coupling 140 rotates together with it and the first angled engaging face 148a on the flange deflecting dog 147 contacts the angled face 184a of the barrier 180. Further rotation of the drive coupling 140 causes the flange deflecting dog 147 to ride along the angled engaging face 184a and onto the inner track 182, thereby deflecting the flexible flange portion 146 towards the indexing wheel.

The flexible flange portion 146 has a wedge-shaped drive dog 149 that upstands inwardly towards the indexing wheel. The drive dog 149 engages between two spokes 161 of the indexing wheel 160 when the flexible flange portion 146 has been deflected inwardly, so that the indexing wheel 160 is now driven by the drive coupling 140.

At the point when the flange deflecting dog 147 reaches the end of the inner track 182, it falls off the barrier 180. The resilience of the flexible flange portion 146 causes it to return to its neutral position, so that the drive dog 149 is no longer engaged between the spokes 161 of the indexing wheel 160. This is the end of the first part of the opening stroke of the outer cover. The circumferential length of the barrier 180 controls the extent of rotation of the indexing wheel 160 relative to the extent of rotation of the drive gear 120. In an embodiment where two blisters are indexed and pierced on each actuation, the length of the barrier is chosen so that the indexing wheel is rotated through the correct angle to move the next, unused blister, into alignment with the blister piercing element during the opening stroke. Thus when the drive coupling is rotated further during the second part of the opening stroke, drive to the indexing wheel is disengaged. Despite continued rotation of the outer cover and drive gear in the same direction, the indexing wheel is stationary. This allows the blisters to be pierced while the blister strip is stationary, in a manner which is explained below.

As the outer cover is returned to the closed position, the first drive gear and first drive coupling rotate back in the opposite direction. The second angled surface 148b of the flange deflecting dog 147 contacts the second angled face of the barrier 184b, so that the flange deflecting dog 147 rides onto the other side of the barrier 180 and travels along the outer track 182, thereby causing the flexible flange portion 146 to deflect outwardly away from the indexing wheel 160. This enables the drive coupling 140 to rotate in the opposite direction without any drive from the first drive gear 120 to the indexing wheel 160.

So far, the mechanism is the same as that of WO 13/175177. However, in WO 13/175177 the blister strip is stationary while the outer cover is closed, whereas in this embodiment of the invention, the second actuator gear 110, idler gear wheel 150, second drive gear 130 and second drive coupling 141 also cause the blister strip also to be indexed as the outer cover is closed.

The second drive coupling 141 interacts with the second track formation in essentially the same manner as the first drive coupling and track formation, except that the second drive coupling 141 is disengaged from the indexing wheel 160 during the opening stroke and engages with the indexing wheel 160 during the second part of the closing stroke.

As the user closes the outer cover from the fully open position, in the first part of the closing movement, the piercing elements are removed from the blisters. The second actuator gear segment 112 drives the idler gear 150, which in turn drives the second drive gear 130 and the second drive coupling 141. However, because the second drive coupling 141 is not engaged with the indexing wheel 160, the blister strip remains stationery. At the start of the second part of the closing stroke, second drive coupling 141 engages the indexing wheel 160 in the same manner as the first drive coupling 140 did during the first part of the opening stroke. Thus further closing the outer cover causes the indexing wheel to drive the blister strip. The idler gear 150 reverses the sense of rotation of the second drive gear 130 relative to the second actuator gear 110. The indexing wheel 160 is therefore rotated in the same sense as during the opening stroke, even though the outer cover and the second actuator gear rotate in the opposite sense. Thus the blister strip is indexed forwards, not backwards, by the closing of the cover.

Just before the outer cover reaches the fully closed position, the second drive coupling 141 disengages from the indexing wheel 160 in the same manner as the first drive coupling 140 did at the end of the first part of the forward stroke.

Thus the two drive couplings combine to change the gearing between the outer cover and the indexing wheel from drive during the first part of the opening stroke, into neutral during the second part of the opening stroke and the first part of the closing stroke, then into drive during the second part of closing and finally into neutral again in the fully closed position. Consequently, the blister strip is indexed forwards both during opening and closing. For example, the strip may be indexed by one blister on opening and by a second on closing, so that the next two unopened blisters are correctly positioned relative to the piercing elements, ready for the next use.

The outer cover cooperates with the piercer so that rotation of the outer cover during the second part of the opening stroke causes the piercer to pivot relative to the housing to puncture the lid of the aligned blisters, in essentially the same manner as also described in detail in WO 13/175177. In brief, this is achieved by means of a cam 9 located on the mouthpiece support member 5 which cooperates with the cam slot 8 in the outer cover 3. As shown in FIG. 1B, the cam slot has an arcuate portion 8a centered on axis P and a leg portion 8b. During rotation of the outer cover 3 through the first part of the opening stroke, the cam 9 slides along the arcuate portion 8a of the cam slot without causing any movement of the mouthpiece support member 5 because the arcuate portion has the same axis as the outer cover. However, during the second part of the rotation of the outer cover, the cam 9 reaches the leg portion 8b and engages the side walls of the cam slot so as to cause the mouthpiece support member 5 to pivot about axis Q, thereby pulling the piercing elements into the lids of the aligned blisters and piercing them. When the outer cover is rotated back through the first part of the closing stroke, the cam 9 travels back along the leg portion 8b of the cam slot, causing the mouthpiece support member 5 to pivot back to its initial position, thereby lifting the piercing elements out of the pierced blisters. During rotation of the outer cover through the second part of the closing stroke, the cam slides along the arcuate portion 8a of the cam slot without causing any movement of the mouthpiece support member 5. In an alternative configuration, the cam could project from the inside of the outer cover into a cam slot on the mouthpiece support member.

The first actuator gear may include a cantilever 105 which contacts a ramp 14 (shown in FIG. 1C) on the housing 2 so that a biasing force is applied by the ramp 14 to the cantilever 105 during rotation of the first actuator gear 100, as described in WO 13/175176. The shape of the ramp is designed so that the degree of deflection of the cantilever, and hence the biasing force changes with the angle of rotation of the actuator gear. As the degree of deflection of the cantilever changes, the torque that must be applied to the outer cover changes, thereby producing a tactile effect experienced by the user. The first actuator gear may also include a detent arm 106, which has an enlarged head that engages with a detent peg on the housing (not visible in FIG. 1C) when the outer cover is in the closed position. When the user begins to open the outer cover, a small torque must initially be applied to deflect the detent arm as the head passes over the detent peg. In addition to providing a slight resistance to initial movement of the outer cover which prevents accidental opening, the enlarged head is shaped so that the detent mechanism also pulls the cover in to the closed position at the end of the closing stroke. The detent arm can be arranged to generate a 'click' at end of the second part of the closing stroke, and so provide an audible and palpable signal to the user that the outer cover has been fully closed.

Figure 5A:
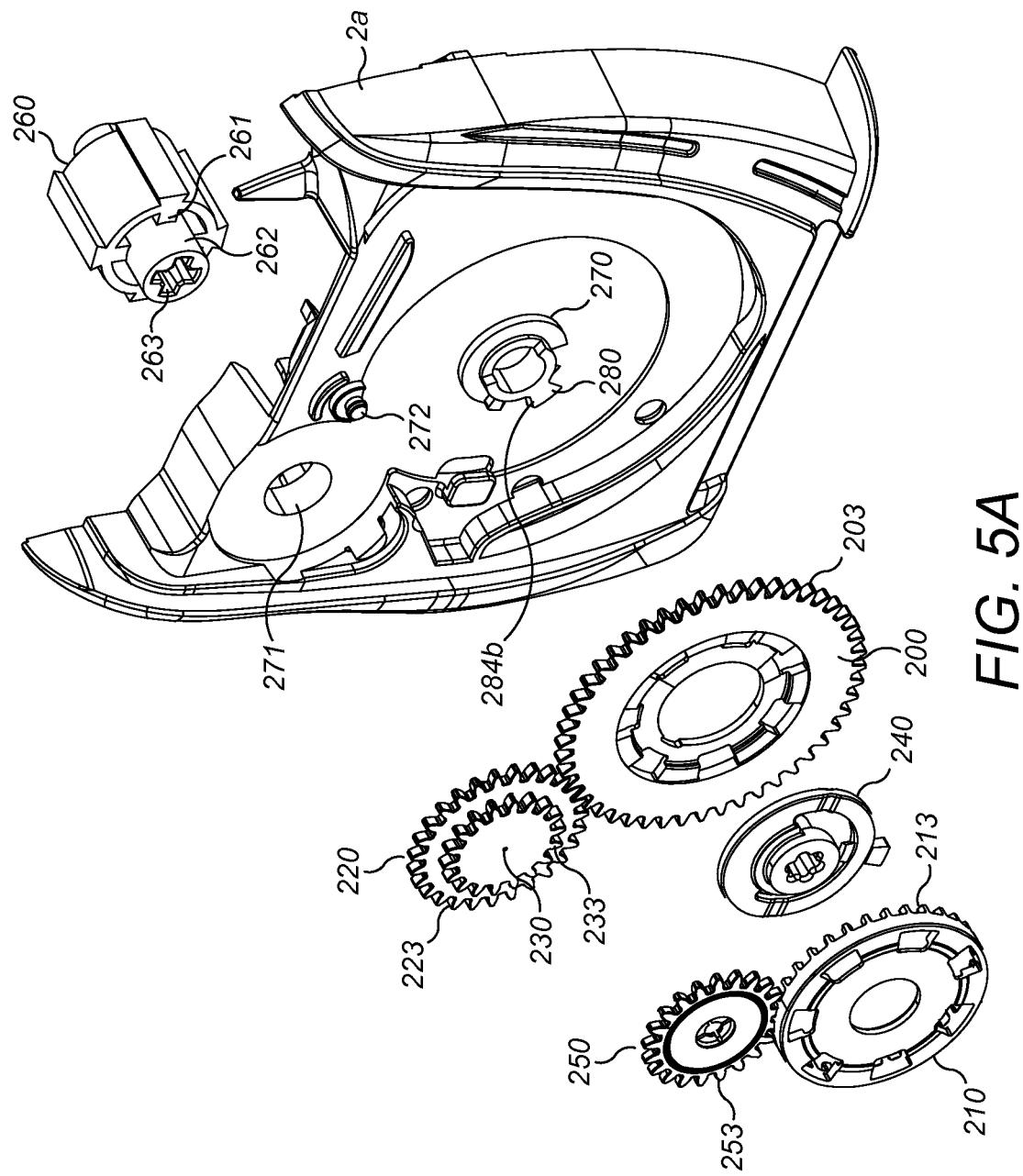
FIGS. 5A and 5B show expanded and assembled views of the indexing mechanism of the second embodiment.
Figure 5B:
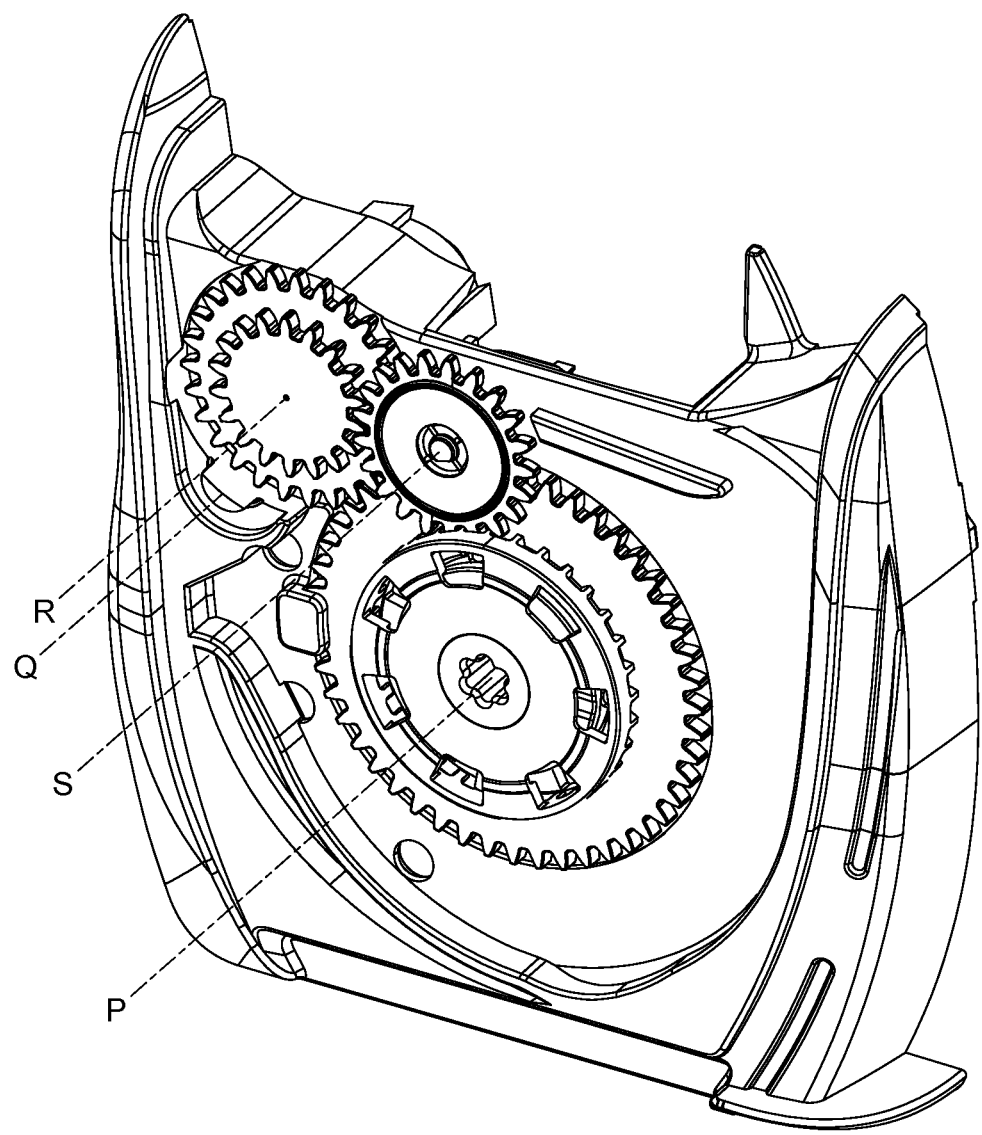
Figure 6:
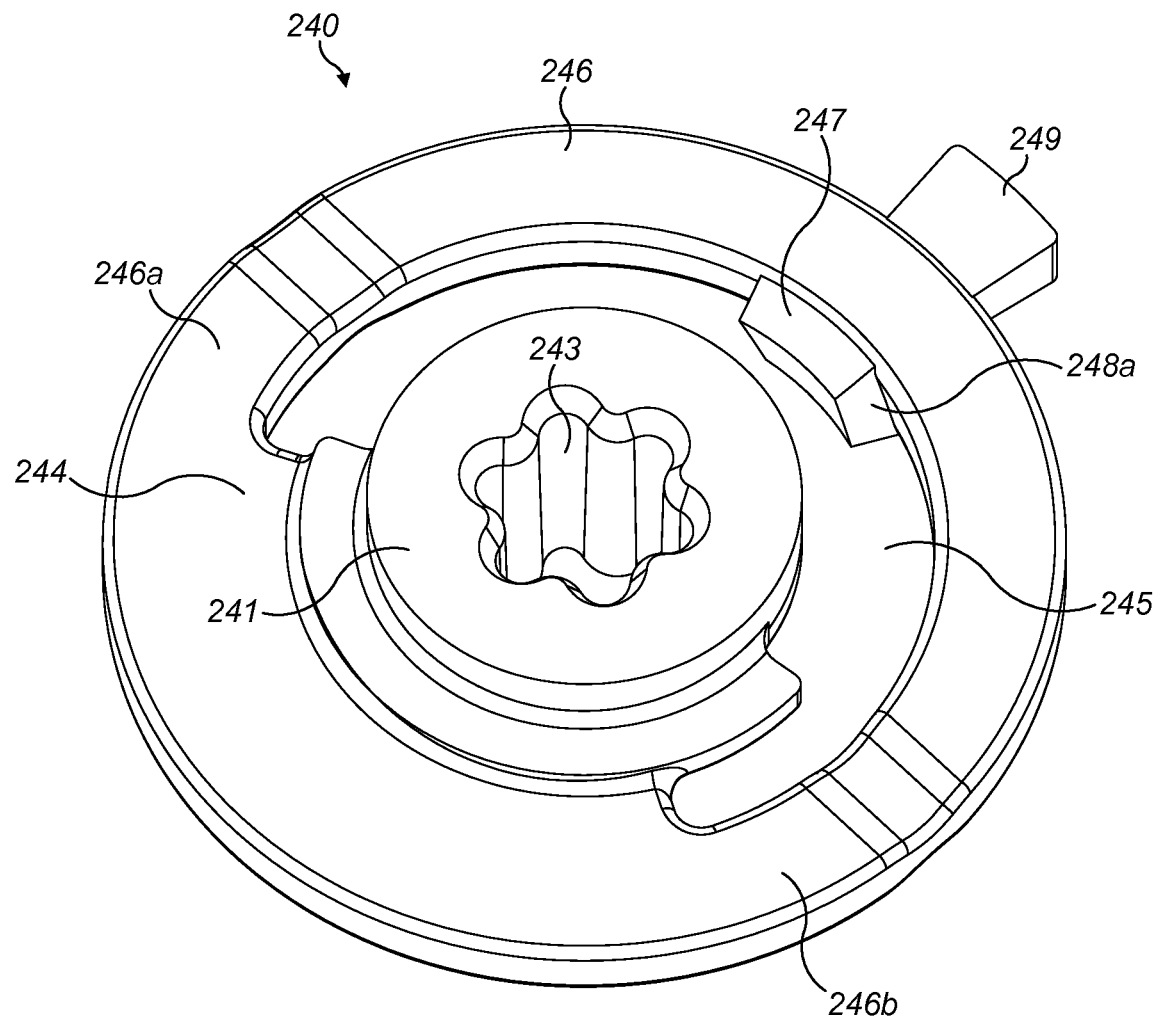
FIG. 6 shows the drive coupling of the second embodiment.

FIGS. 5 to 7 show the indexing mechanism of a second embodiment of an inhaler of the invention. In this embodiment, the opening and closing gears are situated on the same side of the housing and there is only one drive coupling, which couples to both the opening and closing drive gears (i.e. a dual drive coupling).

The dual drive coupling serves the same function as the separate drive couplings of in the first embodiment, i.e. to change the gearing between the outer cover and the indexing wheel from drive during the first part of the opening stroke, into neutral during the second part of opening and the first part of closing, and then into drive during the second part of closing. However, the dual drive coupling performs this function in a different way, by selectively coupling the outer cover to the actuator gears instead of selectively coupling the drive gears to the indexing wheel. Having only one drive coupling has the advantage that there is no possibility of two drive couplings becoming out of synchronization, which could in principle occur in the first embodiment.

FIGS. 5A and 5B show expanded and assembled views of the mechanism, together with one shell portion of the housing 2a. The mechanism has a first actuator gear 200, a first drive gear 220, a blister strip indexing wheel 260, a second drive gear 230, an idler gear wheel 250, a second actuator gear 210 and a dual drive coupling 240 located between the first and second actuator gears. There are two important differences in the gears compared to the first embodiment.

Firstly, both drive gears are permanently coupled to the indexing wheel. Thus, as shown in FIG. 5A, the first and second drive gears can be linked together or formed as a single component. Consequently, the gear train formed by the first actuator gear 200, first drive gear 220, indexing wheel 260, second drive gear 230, idler gear 250 and second actuator gear 210 is always connected. However, unlike the first embodiment, the actuator gears are not always coupled to the outer cover.

Secondly, each gear rotates in the same sense during both opening and closing, whereas in the first embodiment they rotate in one sense during opening and in the opposite sense during closing. Thus all of the gears must be full gear wheels, rather than just gear segments. In order that the angle through which the indexing wheel rotates is the same on both opening and closing, the gear ratio between the actuator gear and drive gear must be the same for each pair. The gear ratio determines the angle through which the indexing wheel is rotated on each actuation.

As shown in FIG. 5B, Axes P, Q, R and S are located in the same positions on the housing as in the first embodiment. An actuator gear axle 270 for mounting the first and second actuator gears and the drive coupling is located on axis P. A track formation 280 extends radially outwards from the axle 270. A circular hole 271 in the housing provides a bearing surface for mounting the drive gears and indexing wheel on axis R. An idler gear wheel axle 272 is located on axis S.

The inner layer of the mechanism (adjacent to the housing) consists of the first actuator gear 200 and the first drive gear 220. The first actuator gear 200 is mounted for rotation on the actuator gear axle 270. The first drive gear 220 is mounted on the indexing wheel 260, by means of a cruciform shaft on the first drive gear wheel (not visible in this Figure) which extends through hole 271 and fits into a corresponding cruciform slot 263 inside the hub 262 of the indexing wheel 260. The first drive gear 220 therefore rotates together with the indexing wheel 260 about axis R. The first actuator gear 200 engages with the first drive gear 220 via teeth 203, 223 on each wheel.

The outer layer consists of the second actuator gear 210, the second drive gear 230 and the idler gear 250. The second actuator gear 210 is co-axial with the first actuator gear and is also mounted for rotation about axis P on the actuator gear axle 270. The second drive gear 230 is co-axial with the first drive gear 210 and is also mounted for rotation about axis R. The second drive gear may be formed (e.g. moulded) as a single component with the first drive gear, or may be a separate component which is fixedly mounted on the first drive gear. The second actuator gear 210 and second drive gear 230 have smaller radii than the first actuator gear 200 and drive gear 220 respectively. Consequently, their teeth 213, 233 do not engage with each other. However, the second actuator and drive gears both engage with the teeth 253 of the idler gear 250 which is mounted on the idler gear wheel axle 272 for rotation about axis S. Consequently, the second actuator gear and second drive gear rotate in the same sense as each other, and the opposite sense to the idler gear.

The drive coupling 240 is located between the first and second actuator gear wheels 200, 210. The function of the drive coupling 240 is to selectively couple the outer cover to the first actuator gear 200 during the first part of opening, to uncouple the outer cover from both actuator gears during insertion and removal of the piercing elements and to couple the outer cover to the second actuator gear during the second part of closing. Since the first and second actuator gears rotate in opposite senses, rotating the outer cover in either direction (opening or closing) always causes the drive gears to rotate in the same direction, and hence the indexing wheel always moves the blister strip forwards.

Since the first and second drive gears are fixedly linked to each other (via the indexing wheel), the whole gear train (first actuator gear-first drive gear-indexing wheel-second drive gear-idler gear-second actuator gear) is always engaged (i.e. linked together). The first and second actuator gears rotate in opposite senses because of the idler gear.

FIG. 6A shows the drive coupling 240. It has a hub 241 with a star-shaped central recess 243 and a circular flange 244 that extends radially from the hub 241. A corresponding star-shaped peg on the inside of the outer cover fits into the central recess 243. The outer cover is thereby fixedly linked to the drive coupling so that rotation of the outer cover causes the drive coupling to rotate.

The flange 244 has a cut-away arcuate opening 245 where it joins the hub 241 so that approximately half 246 of the flange 244 is not directly attached to the hub 241 but only to the other portion of the flange 244 at each of its ends 246a, 246b. As a result, this portion 246 of the flange 244 is flexible and can be deflected out of the plane of the flange 244 towards the first or second actuator gear when force is applied to it. The flange 244 is made from a resilient material so that when the deflected flexible flange portion 246 is released, it returns to its neutral position, in which it is coplanar with the remaining fixed portion of the flange 244.

The flexible flange portion 246 has an integrally formed flange deflecting dog 247 which projects radially inwards into the arcuate opening 245 mid-way along it. The flange deflecting dog 247 has first and second angled engaging faces 248a, 248b on opposite ends, only one of which is visible in FIG. 6. It functions in essentially the same way as the flange deflecting dog in the first embodiment. Opposite the flange deflecting dog, a drive dog 249 extends a short distance radially outwards from the outer edge of the flexible flange portion 246. This drives both the first and second actuator gears, in a manner which will be described below.

The track formation 280 is rhomboid in cross-section, so that it has an angled engaging face 284a, 284b at either end. These guide the flange deflecting dog 247 along one side of the track formation 280 as the outer cover is opened and back along the opposite side as it is closed, in the same manner as described above for the first embodiment. As the flange deflecting dog 247 engages with, and moves around, the track formation 280, the flexible flange portion 246 is deflected so that the drive dog 249 engages and disengages with spokes 204, 214 on the first and second actuator gears 200, 210 to drive them.

Figure 7A:
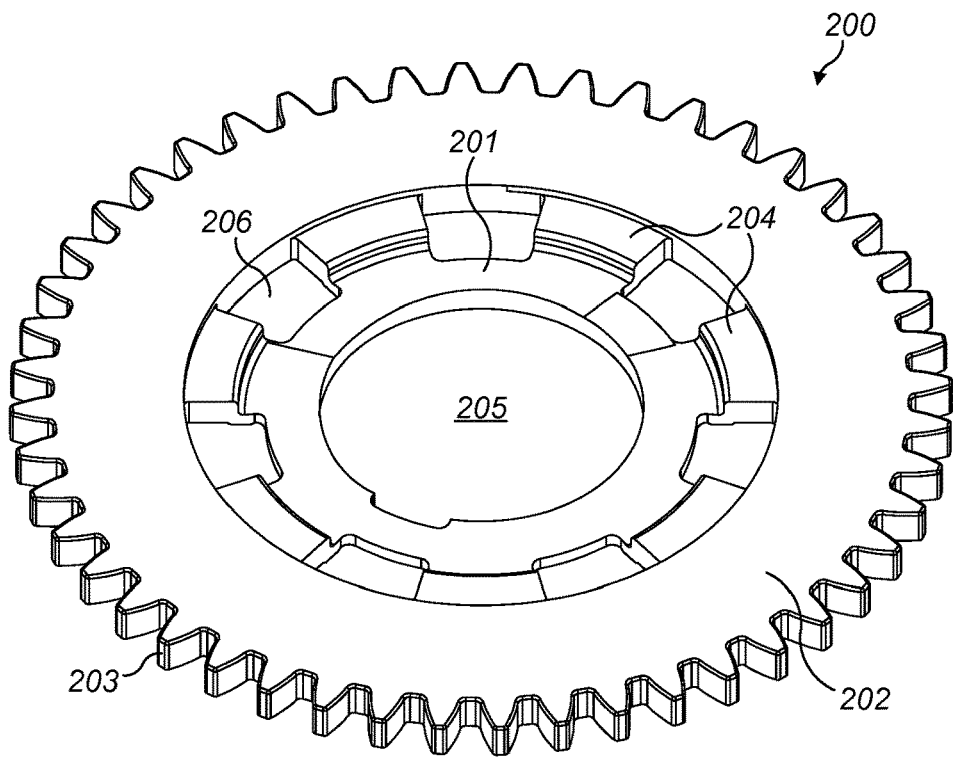
FIGS. 7A and 7B show the first and second actuator gears.
Figure 7B:
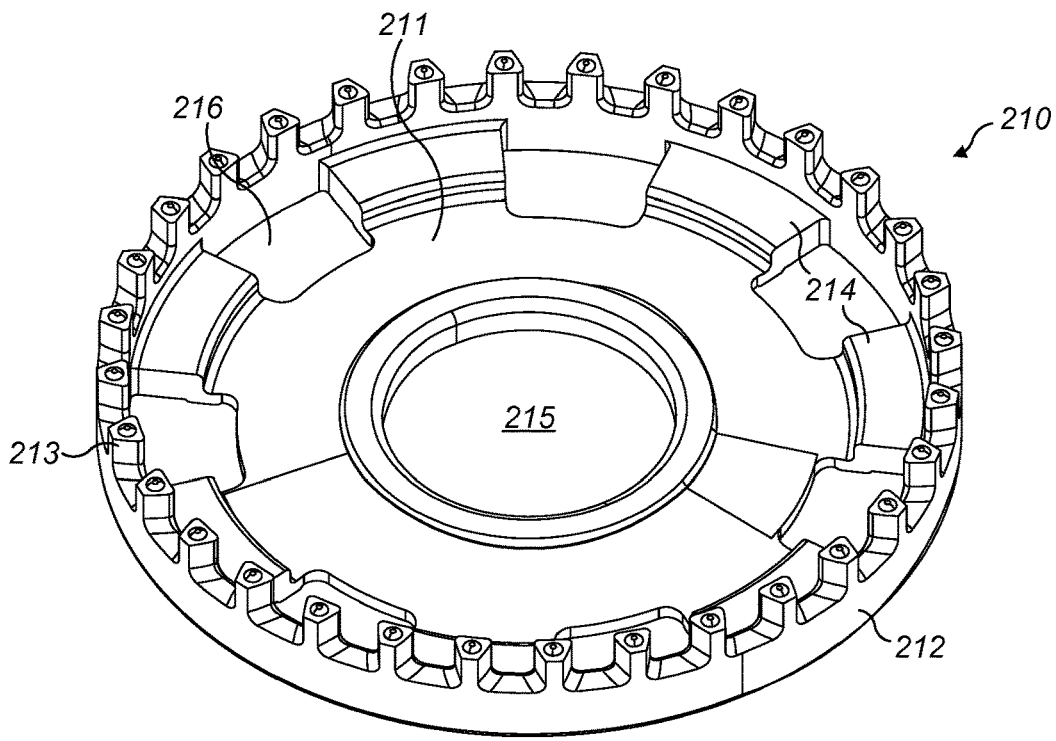

FIGS. 7A and 7B show the first and second actuator gears 200, 210 respectively, each viewed from the side adjacent to the drive coupling. The actuator gears 200, 210 are formed as wheels with a hub 201, 211, and a rim 202, 212 from which the teeth 203, 213 protrude. The hub and rim are connected by spokes 204, 214. Each hub 201, 211 has a central hole 205, 215 for mounting the actuator gear on the actuator gear axle 270.

The drive dog 249 is displaced into a gap 206, 216 between two of the spokes 204, 214 when the flexible flange portion 246 has been deflected, so that the actuator gear 200, 210 is driven by the drive coupling 240.

When the outer cover is in the fully closed position, the flange deflecting dog 247 is adjacent to the first end of the track formation 280 and lies in the same (neutral) plane. The drive dog 249 is also lies in this plane. As the outer cover is opened, the drive coupling is rotated so that the first angled engaging face 248a of the flange deflecting dog 247 comes into contact with the first angled engaging face 284a of the track formation 280. Further rotation of the drive coupling 240 causes the flange deflecting dog 247 to ride along the angled engaging face 284a to the inner side of the track formation 280 and along the first track. The drive dog 249 is also deflected, into a gap 206 between two of the spokes 204 on the first actuator gear 200.

Opening the outer cover further causes the drive coupling to rotate, so that the flange deflecting dog 247 rides along the inner side of the track formation 280. The drive dog 249 comes into contact with the spoke 204 in front of it, so that the first actuator gear 200 is driven by the drive coupling 240, thereby causing the first drive gear and indexing wheel to rotate to move the blister strip as described above.

At the point when the flange deflecting dog 247 passes the end of the track formation 280, it falls off. The resilience of the flexible flange portion 246 causes it to return to its neutral position, so that the drive dog 249 moves out of alignment with the spokes 204 of the first actuator gear 200. The drive coupling thus returns to neutral. This is the end of the first part of the opening stroke of the outer cover. Further rotation of the outer cover through the second part of the opening stroke causes the flange deflecting dog 247 to rotate further, whilst remaining in the neutral plane. Since the drive coupling is disengaged, the blister strip is not indexed any further. The further rotation of the outer cover causes the piercing elements to pierce the aligned blisters, as described above.

After inhalation, the user closes the outer cover. Initially, the flange deflecting dog 247 travels back towards the track formation 280, during which the piercing elements are removed from the pierced blisters while the drive coupling remains in neutral. The angled engaging faces 248b, 284b deflect the flange deflecting dog 247 onto the other (i.e. outer) side of the track formation 280. The drive dog 249 is deflected outwards into a gap 216 between two of the spokes 214 of the second actuator gear 210.

As the outer cover continues to close, the drive coupling rotates, so that the flange deflecting dog 247 rides along the track formation 280. The drive dog 249 comes into contact with the spoke 214 in front of it, thus driving the second actuator gear 210 and thereby indexing the blister strip forwards, as described above.

When the flange deflecting dog 247 passes the end of the track formation 280, the resilience of the flexible flange portion 246 causes it to return to its neutral position, so that the drive dog 249 moves out of alignment with the spokes 214 of the second actuator gear 210. The drive coupling thus disengages from the second actuator gear, so that it is in neutral when the outer cover is fully closed. Further actuations of the device repeat this cycle.

In the embodiment shown in FIGS. 5 to 7, each actuator gear 200, 210 has seven spokes 204, 214 and the indexing wheel 260 has four spokes 261. The gear ratio between each actuator gear and its corresponding drive gear is chosen so that rotation of the actuator gear 200, 210 through $1/7^{th}$ of a circle (51.4°) causes the indexing wheel 260 to rotate through 90° in order to index the blister strip by one blister, i.e. a gear ratio of 7:4. The outer cover rotates through approximately 90° during opening. During the first few degrees, the drive coupling engages with the first actuator gear. Then, for the next 51.4° the drive coupling drives the first actuator gear and the blister strip is indexed. The final approximately 35° of rotation of the outer cover is used for piercing.

The gear ratio between the actuator gears and their corresponding drive gears can be chosen to index the blister strip by different amounts. For example, in order to move the strip by half a blister pitch or one and a half blister pitches, the gear ratios would be 7:8 and 21:8 respectively.

A different number of spokes could be chosen to adjust the amounts of the outer cover motion that drive indexing and piercing. The number of actuator gear spokes (N) determines the angle through which the actuator gear rotates (360°/N). For example, six spokes corresponds to 60° for indexing and 30° for piercing. There must be at least five spokes-if there were only four spokes, the whole 90° would be used for indexing, leaving nothing for piercing. Six or seven spokes has been found to be preferable. Higher numbers result in smaller gaps between the spokes, which means that there is less angular motion available for indexing, so the user must apply a greater torque.

FIGS. 8 to 12 show the indexing mechanism of a third embodiment of an inhaler of the invention. The third embodiment is similar to the second embodiment, but the dual drive coupling takes a different form.

Figure 8A:
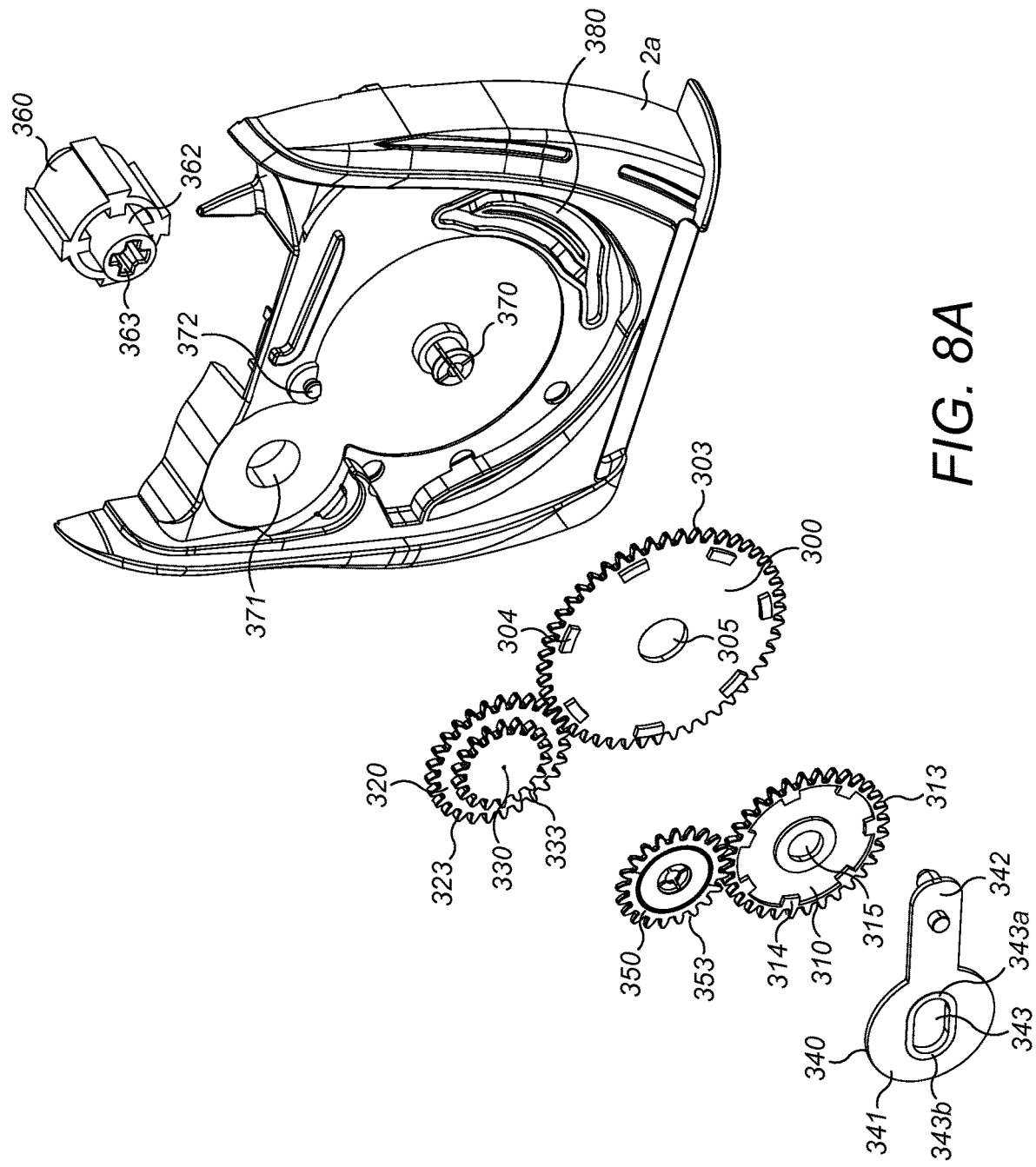
FIGS. 8A and 8B show expanded and assembled views of the indexing mechanism of the third embodiment.
Figure 8B:
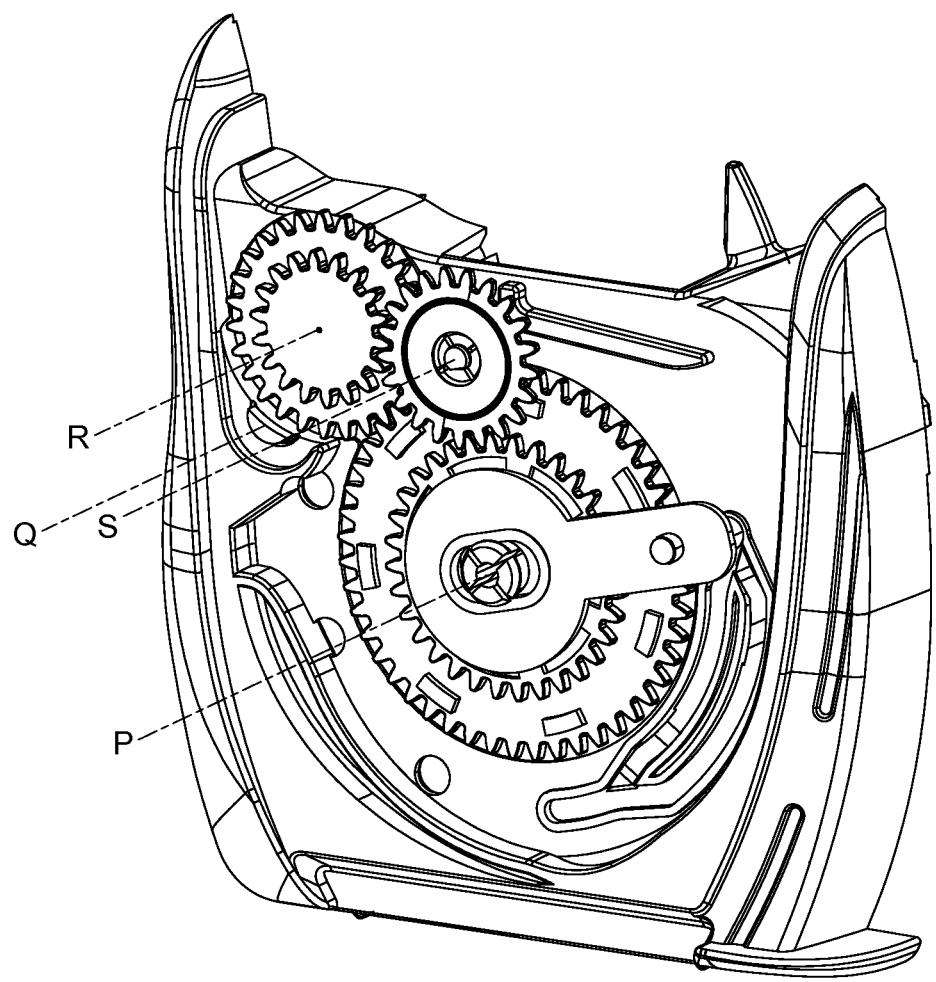

FIGS. 8A and 8B show expanded and assembled views of the indexing mechanism of the third embodiment, together with one shell portion of the housing 2a. The mechanism has a first actuator gear 300, a first drive gear 320, a blister strip indexing wheel 360, a second drive gear 330, an idler gear wheel 350, a second actuator gear 310 and a drive coupling 340 located on the outer side of the mechanism.

As with the second embodiment, both drive gears are permanently coupled to the indexing wheel. Thus, as shown in FIG. 8A, the first and second drive gears can be linked together or formed as a single component. The gear train formed by the first actuator gear 300, first drive gear 320, indexing wheel 360, second drive gear 330, idler gear 350 and second actuator gear 310 is always connected. The drive coupling selectively couples the outer cover to the first or second actuator gear and each gear rotates in the same sense during opening and closing.

As shown in FIG. 8B, axes P, Q, R and S are located in the same positions on the housing as in the previous embodiments. An actuator gear axle 370 for mounting the first and second actuator gears and the drive coupling is located on axis P. A circular hole 371 in the housing provides a bearing surface for mounting the drive gears and indexing wheel on axis R. An idler gear axle 372 is located on axis S. A track 380 is located on the housing to the side of the area occupied by the gear wheels. The track is described further below.

The inner layer of the mechanism (adjacent to the housing) consists of the first actuator gear 300 and the first drive gear 320. The first actuator gear 300 is mounted for rotation on the actuator gear axle 370 by its central hole 305. The first drive gear 320 is mounted on the indexing wheel 360, by means of a cruciform shaft on the first drive gear wheel (not visible in this Figure) which extends through hole 371 and fits into a corresponding cruciform slot 363 inside the hub 362 of the indexing wheel 360. The first drive gear 320 therefore rotates together with the indexing wheel 360 about axis R. The first actuator gear 300 engages with the first drive gear 320 via teeth 303, 323 on each wheel. There are seven equi-angularly spaced actuator gear dogs 304 in the form of blocks which protrude from the outer surface of the first actuator gear 300 and which engage with the drive coupling in a manner that is described below.

The middle layer consists of the second actuator gear 310, the second drive gear 330 and the idler gear 350. The second actuator gear 310 is co-axial with the first actuator gear and is also mounted for rotation about axis P on the actuator gear axle 370 by its central hole 315. The second drive gear 330 is co-axial with the first drive gear 320 and is also mounted for rotation about axis R. The second drive gear may be formed (e.g. moulded) as a single component with the first drive gear, or may be a separate component which is fixedly mounted on the first drive gear. The second actuator gear 310 and second drive gear 330 have smaller radii than the first actuator gear 300 and first drive gear 320 respectively. Consequently, their teeth 313, 333 do not engage with each other. However, the second actuator and drive gears both engage with the idler gear 350 which is mounted on the idler gear wheel axle 372 for rotation about axis S. Consequently, the second actuator gear and second drive gear rotate in the same sense as each other, and the opposite sense to the idler gear. There are seven equi-angularly spaced actuator gear dogs 314 in the form of blocks which protrude from the outer surface of the second actuator gear 310 and which engage with the drive coupling as described below.

Since the first and second drive gears are fixedly linked to each other (via the indexing wheel), the whole gear train (first actuator gear-first drive gear-indexing wheel-second drive gear-idler gear-second actuator gear) is always engaged (linked together). The first and second actuator gears rotate in opposite senses because of the idler gear.

The drive coupling 340 is located on the outer side of the second actuator gear 310 (i.e. adjacent to the outer cover). The function of the drive coupling 340 is to selectively couple the outer cover to the first actuator gear during the first part of opening, to uncouple the outer cover from both actuator gears during insertion and removal of the piercing elements and to couple the outer cover to the second actuator gear during the second part of closing. Since the first and second actuator gears rotate in opposite senses, rotating the outer cover in either direction (opening or closing) always causes the drive gears to rotate in the same direction, and hence the indexing wheel always moves the blister strip forwards.

Figure 9:
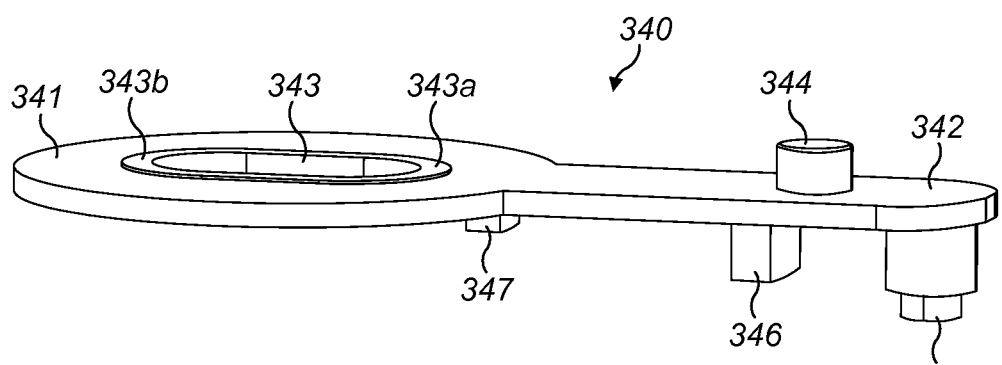
FIG. 9 shows the drive coupling of the third embodiment.

FIG. 9 shows the drive coupling 340 which has a flange 341 and an arm 342. The flange has a slot 343 with straight sides and rounded ends which mounts the drive coupling 340 on the actuator gear axle 370. The slot 343 allows the drive coupling both to rotate about axis P and to translate radially between two drive positions. In the first drive position, the first rounded end 343a of the slot 343 is in contact with the actuator gear axle 370, so that the tip of the arm 342 is at its closest position to axis P. In the second drive position, the second rounded end 343b of the slot is in contact with the axle 370, so that the tip of the arm 342 is at its furthest position from axis P. In between these, when the axle 370 is intermediate between the two ends of the slot, the drive coupling 340 is disengaged, i.e. in neutral.

Figure 10:
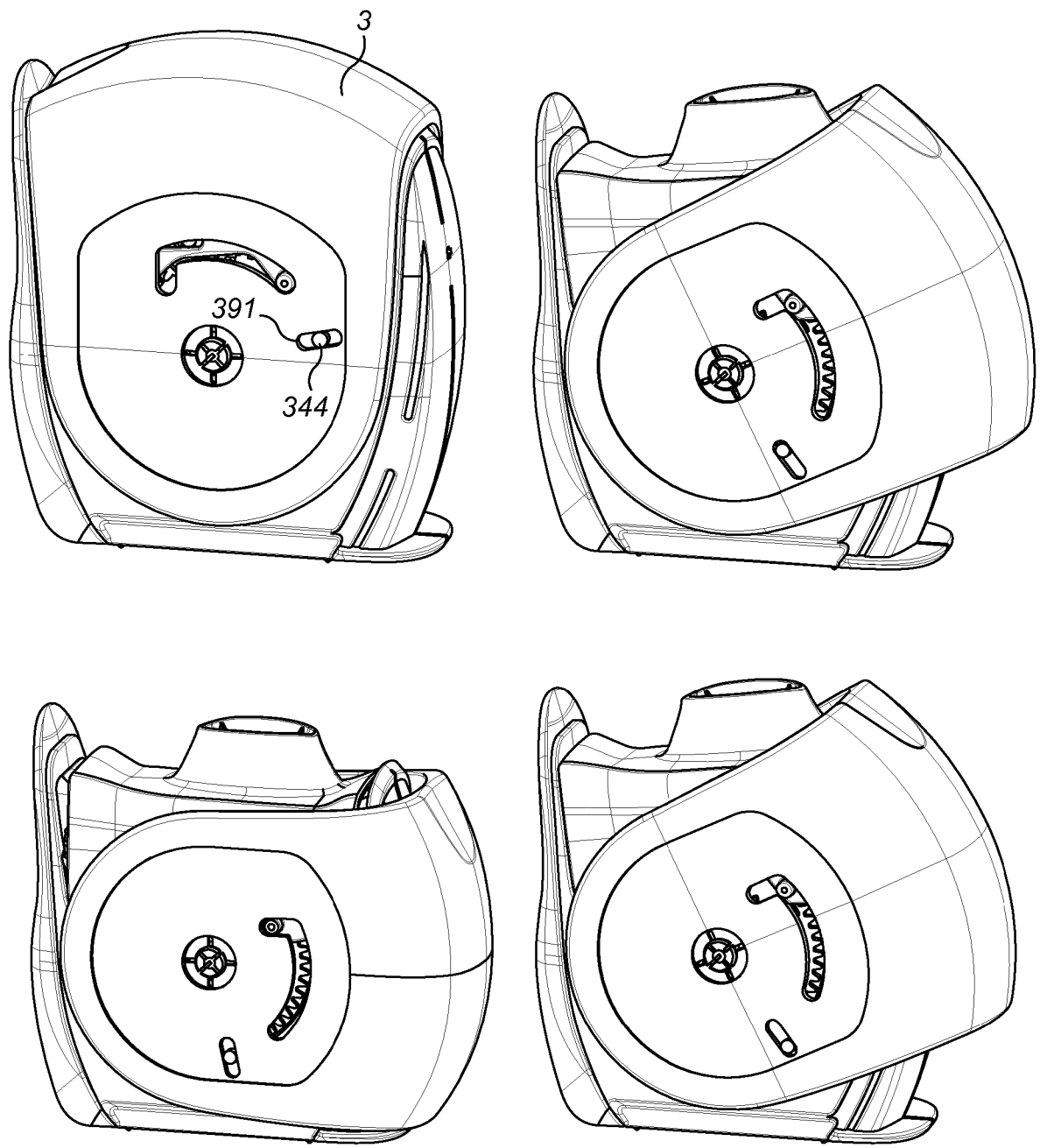
FIG. 10 shows the drive pin which fits in a radial slot in the outer cover.

A drive pin 344 protrudes from the outer side of the arm. The drive pin 344 fits in a radial slot 391 in the outer cover 3, as shown in FIG. 10. The cover slot 391 is the same length as the slot 343 in the drive coupling 340. Thus when the drive coupling 340 moves in the radial direction, the drive pin 344 also moves along the slot 391 in the outer cover 3. FIG. 10A shows the outer cover 3 in the closed position, so that the drive coupling 340 is neutral and the drive pin 344 is in the centre of the slot 391. In FIG. 10B, the outer cover is opening, so that the drive coupling 340 is in the first drive position and the drive pin 344 is at the inner end of the slot 391. FIG. 10C shows the outer cover 3 in the open position, so that the drive coupling 340 is back in neutral and the drive pin 344 is in the centre of the slot 391. In FIG. 10D, the outer cover 3 is closing, so that the drive coupling 340 is in the second drive position and the drive pin 344 is at the outer end of the slot 391. Thus the cover slot 391 pushes against the drive pin 344, and thereby causes the drive coupling 340 to rotate, whichever position the drive pin is in.

As also shown in FIG. 9, a track follower 345 is located on the opposite (inner) side of the drive coupling 340, near the tip of the arm 342. The track follower 345 is a peg which moves around the track 380 on the housing as the outer cover is opened and closed, as will be described in detail below. First and second drive dogs 346, 347 are also located on the inner side of the drive coupling 340. These engage with the actuator gear dogs 304, 314 on the first and second actuator gears when the arm 342 is in the first and second positions respectively, and thereby drive the actuator gears 300, 310, as will also be described in detail below. The second drive dog 347 is shorter (i.e. protrudes a smaller distance from the drive coupling) than the first drive dog 346 because the second actuator gear 310 (with which the second drive dog 347 engages) is located closer to the drive coupling than the first actuator gear 300.

Figure 11A:
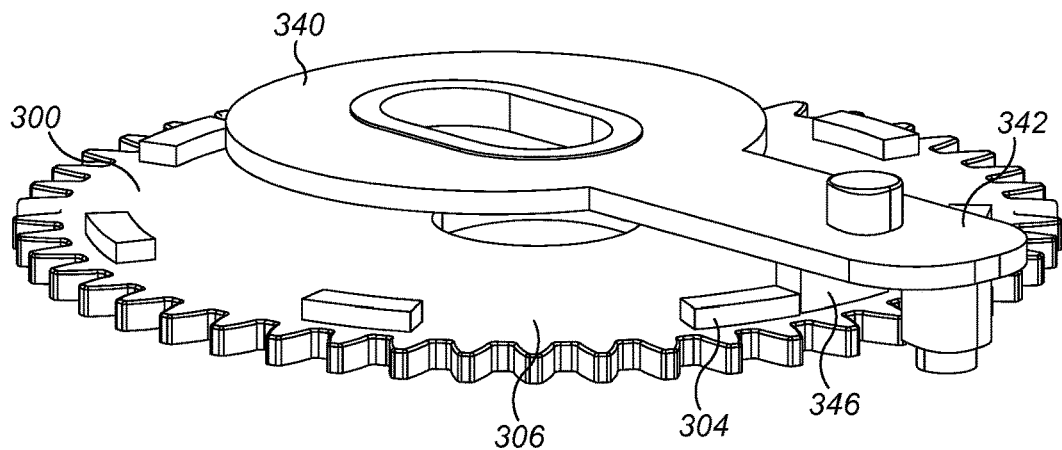
FIGS. 11A, 11B and 11C show the drive dogs on the drive coupling and the actuator gear dogs in the first and second drive positions.

FIG. 11A shows the drive coupling 340 in the first drive position and the first actuator gear 300 (the axle and the second actuator gear, which lies between the drive coupling 340 and the first actuator gear 300, are not shown in this Figure for clarity). In this position, the tip of the arm 342 is at its closest position to axis P; the first drive dog 346 is at the same radius as the first actuator gear dog 304, and the second drive dog (not visible in FIG. 11A) is at a smaller radius than the second actuator gear dog 314. Thus in the first drive position, rotation of the drive coupling 340 causes the first actuator drive dog 346 to push against the first actuator gear dog 304, and hence to drive the first actuator gear 300.

Figure 11B:
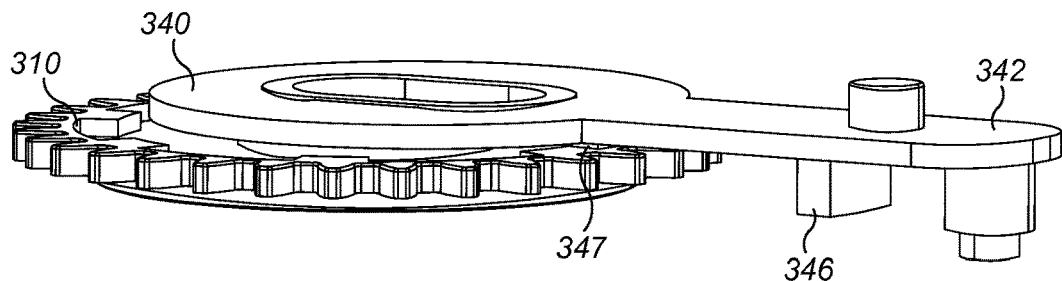
Figure 11C:
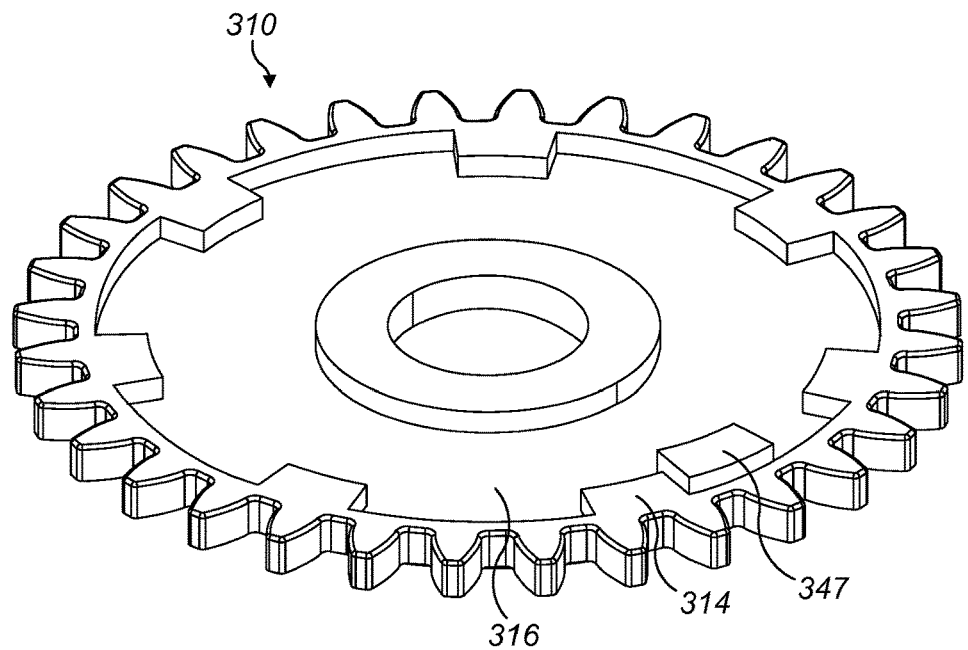

FIG. 11B shows the drive coupling 340 and the second actuator gear 310 in the second drive position. In this position, the tip of the arm 342 is at its furthest position from axis P and the first drive dog 346 is at a larger radius than the first actuator gear dog 304. The second drive dog 347 is mostly hidden FIG. 11B, but is shown in FIG. 11C in which the other parts of the drive coupling have been removed for illustration. The second drive dog 347 is at the same radius as the second actuator gear dog 314. Consequently, in the second drive position, rotation of the drive coupling causes the second actuator drive dog 347 to push against the second actuator gear dog 314, and hence to drive the second actuator gear 310.

The actuator gear dogs therefore serve the same function as the spokes on the actuator gears in the previous embodiment.

FIG. 12 shows the drive coupling 340 in different positions around the track 380 during one full opening and closing cycle. The track has a central barrier 381 which lies between and separates a first (inner, opening) track portion 382 and a second (outer, closing) track portion 383. Both track portions 382, 383 are arcs of circles centered on axis P. The radius of the outer track portion 383 is equal to the radius of the inner track portion 382 plus the length of the drive coupling slot 343. Both the inner and outer tracks have short straight sections at each end 382a, 382b, 383a, 383b. These meet at a radius halfway between the radii of the inner and outer track portions. At one end, a neutral (piercing) track portion 384 extends beyond the ends of the inner and outer tracks 382b, 383b from the point at which the straight sections meet. The central barrier 381 tapers to a point at each end 381a, 381b. A wall 385 surrounds the track portions 382, 383, 384.

The inner track 382 has a cut-away opening 386 which extends from approximately the mid-point to its second end 382b along both sides (i.e. adjacent to the central barrier 381 on one side and adjacent to the wall 385 on the other), and across the second end 382b of the inner track, in line with the tapered outer side of the central barrier 381. The cut-away opening defines a flexible portion 387 of the inner track which is not directly attached to the housing on three sides and which can be deflected when force is applied to it. The track 382 is made from a resilient material so that when the deflected flexible portion 387 is released, it returns to its original position. The flexible portion 387 therefore acts as a leaf spring. Moreover, the flexible portion is shaped so that it slopes outwards (i.e. out of the plane of the paper in FIG. 12) from the point where is joined to the inner track to its free end. The end of the flexible portion 387 consequently forms a protruding lip 387a. The outer track 383 similarly has a cut-away opening 388 from approximately its mid-point to its first end 383a which forms a flexible portion 389 with a lip 389a.

Figure 12A:
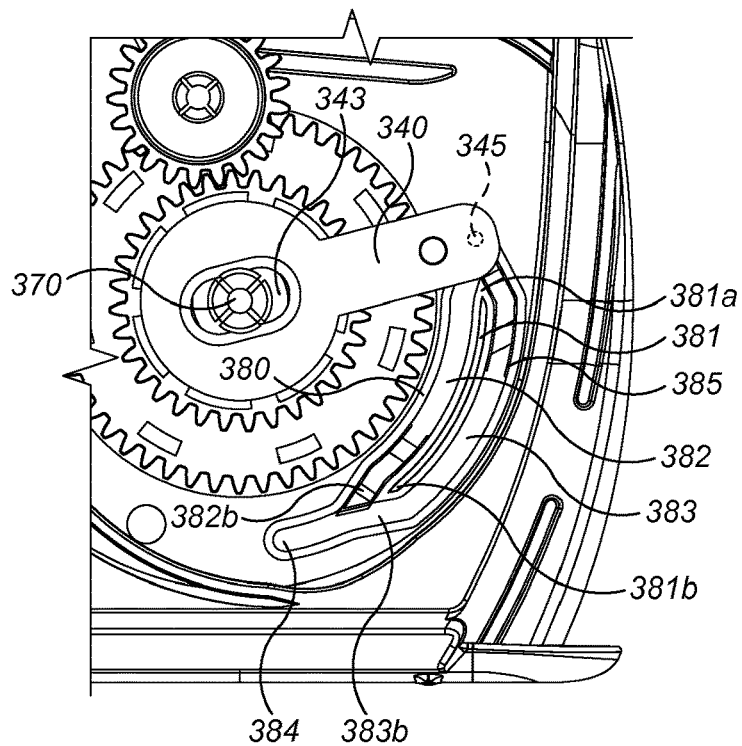
FIG. 12 shows the track formation and the drive coupling in different positions during one full opening and closing cycle.

FIG. 12A shows the configuration when the outer cover is fully closed. The track follower 345 is hidden beneath the arm of the drive coupling in this view; however, its position is indicated in FIG. 12 by a dashed circle. The track follower 345 is at the point where the straight sections of the inner and outer tracks meet at their first ends 382a, 383a, i.e. at the intermediate radius, so the drive coupling is in the position where the actuator gear axle 370 is at the mid-point of the slot 343. In this position, the drive dogs 346, 347 are not at the same radius as their corresponding actuator gear dogs 304, 314 so the drive coupling 340 is in neutral.

Figure 12B:
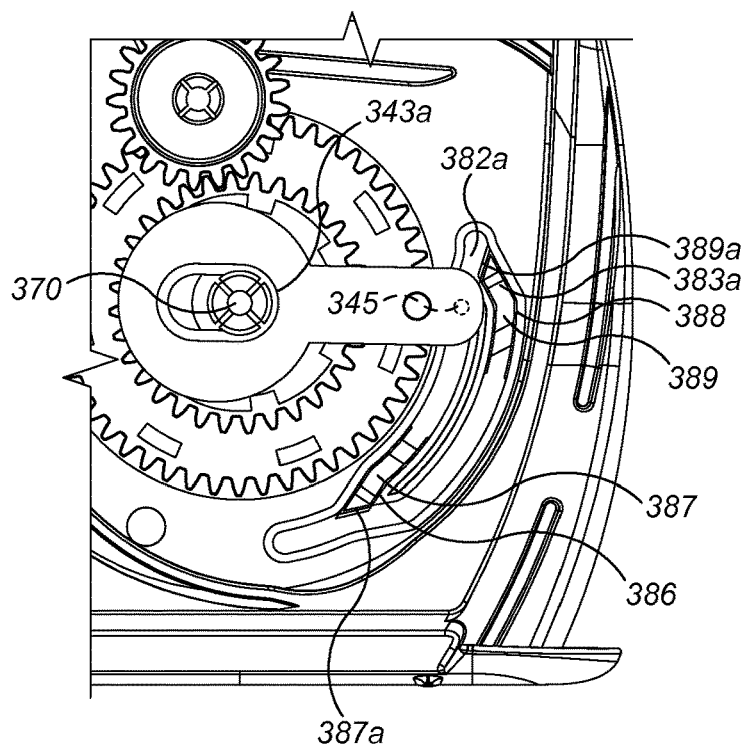

As the outer cover is opened it pushes on the drive pin 344 which causes the drive coupling 343 to rotate. The track follower 345 initially moves along the inner short straight section at the first end of the inner track 382a. The lip 389a guides the track follower 345 onto the inner track 382 and ensures that it does not go onto the outer track 383. The track follower 345 then contacts the tapered portion 381a of the central barrier 381, which pushes the track follower 345, and hence the drive coupling 340 radially inwards until the first end 343a of the slot 343 abuts the actuator gear axle 370. The first drive dog 346 passes into one of the gaps 306 between the actuator gear dogs 304 on the first actuator gear 300. The second drive dog 347 is located at a smaller radius than the second actuator gear dogs 314, so cannot come into contact with them. This configuration is shown in FIG. 12B.

Continuing to open the outer cover causes the drive coupling 343 to rotate further. The track follower 345 is confined by the central barrier 381 and surrounding wall 385 to move along the inner track 382. The first drive dog 346 is at the same radius as the first actuator gear dogs 304 and comes into contact with the adjacent one. This drives the first actuator gear 300, thereby indexing the blister strip, as described above.

Figure 12C:
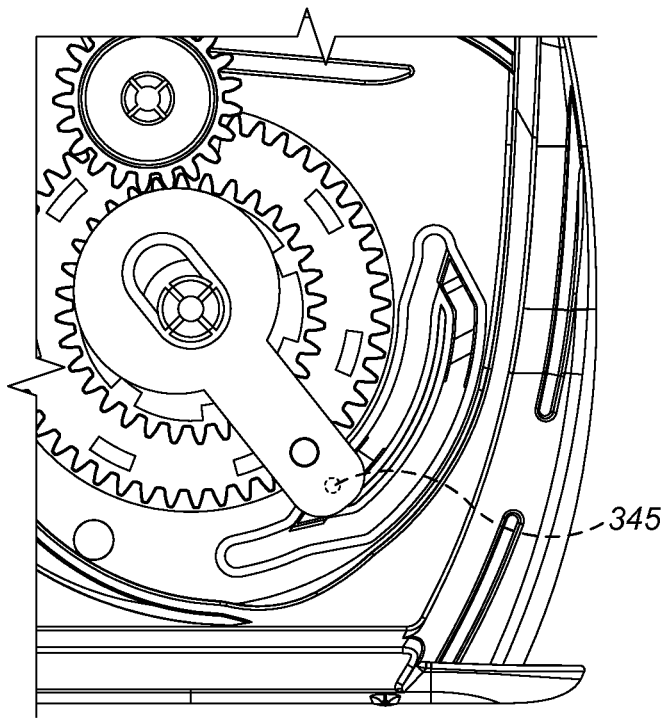

FIG. 12C shows the configuration at the point at which the track follower 345 approaches the end of the inner track 382b. This corresponds to the end of the first part of the opening stroke of the outer cover. The track follower 345 pushes the flexible portion 387 inwards (i.e. into the plane of the paper in FIG. 12) so that the flexible portion 387 is level with the rest of the track. The track follower 345 thereby passes over the flexible portion 387. At the same time, the surrounding wall 385 of the short straight section guides the track follower 345 and hence the drive coupling 340 radially outwards to a neutral position at a radius intermediate between the inner and outer arcuate track portions. Once the track follower 345 has passed over the flexible portion 387 it moves onto the piercing track 384 and the flexible portion 387 springs back to its original position.

Figure 12D:
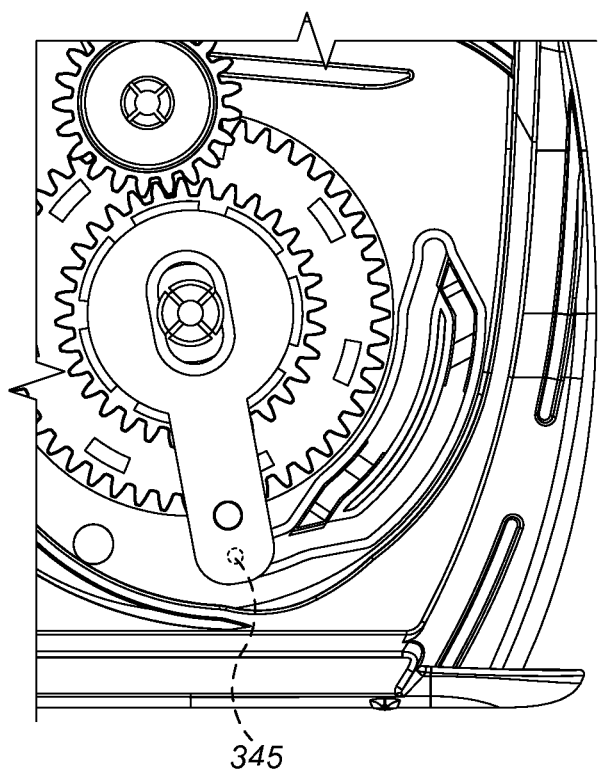

At the end of the inner track portion 382b, the actuator gear axle 370 is halfway along the slot 343 in the drive coupling 340 and the first drive dog 346 has been moved out of radial alignment with the first actuator gear dogs 304. The drive coupling 340 is thus in neutral. Further rotation of the outer cover (though the second part of the opening stroke) causes the track follower 345 to move along the piercing track 384. Since the drive coupling 340 is in neutral, the outer cover is not connected to the gears so the blister strip is not indexed any further. However, the rotation of the outer cover through the second part of the opening stroke motion causes the piercer to pierce the aligned blisters, as described above. FIG. 12D shows the configuration at the point at which the outer cover is fully open and the piercing elements have entered the aligned blisters.

After inhalation, the user closes the outer cover. Initially, the track follower 345 travels back along the piercing track 384, during which the piercer is removed from the pierced blisters while the drive coupling remains in neutral. Instead of returning along the inner track 381, the raised lip 387a of the flexible portion 387 of the inner track 382 guides the track follower 345 to the outer side of the central barrier 381 and onto the outer track 384. In an analogous manner to that described above with reference to FIGS. 12B and 12C, the drive coupling 340 is pushed radially outwards until the second end of the slot 343b abuts the actuator gear axle 370. The second drive dog 347 moves radially outwards into a gap 316 between two of the second actuator gear dogs 314, so that it is at the same radius. The first drive dog 346 is now located at a larger radius than the first actuator gear dogs 304, so cannot come into contact with them.

Figure 12E:
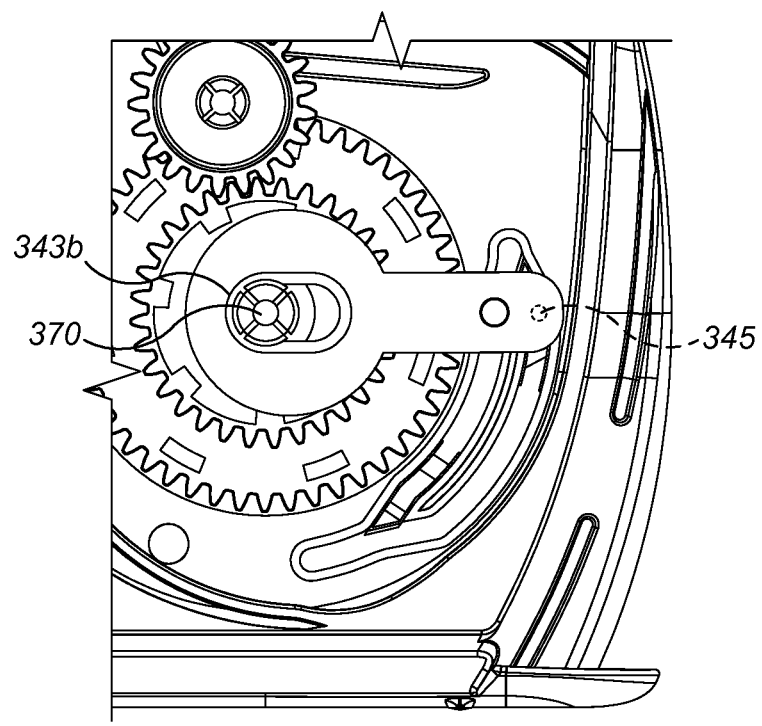

Further closing the outer cover causes the track follower 345 to move along the outer track 383 and the second drive dog 347 to contact the adjacent second actuator gear dog 314, thereby causing the second actuator gear 310 to rotate. This in turn indexes the blister strip forwards. FIG. 12E shows the configuration when the track follower 345 approaches the end of the outer track 383a.

In the final part of the closing stroke of the outer cover, the track follower 345 pushes inwards on the flexible portion 389 so that it is level with the rest of the track. After the track follower 345 has passed over the lip 389a of the flexible portion 389, the flexible portion 389 springs back to its original position. At the same time, the track follower 345 moves along the short straight section at the end 383a of the outer track 383 which causes the second drive dog 347 to disengage from the second actuator gear dogs 314 so that the drive coupling 340 returns to neutral. With the outer cover in the fully closed position, the drive coupling has returned to the initial, neutral position (FIG. 12A). Further operations of the device repeat this cycle. FIGS. 13 to 16 show a fourth embodiment, in which (like the first embodiment), the opening and closing gears are situated on opposite sides of the housing. Similarly, the actuator gears are always coupled to the outer cover and the drive gears are selectively coupled to the indexing wheel. However, in this embodiment there are no drive couplings between the drive gears and the indexing wheel. Instead, the drive gears themselves engage and disengage with the indexing wheel in a manner which is described below.

Figure 13A:
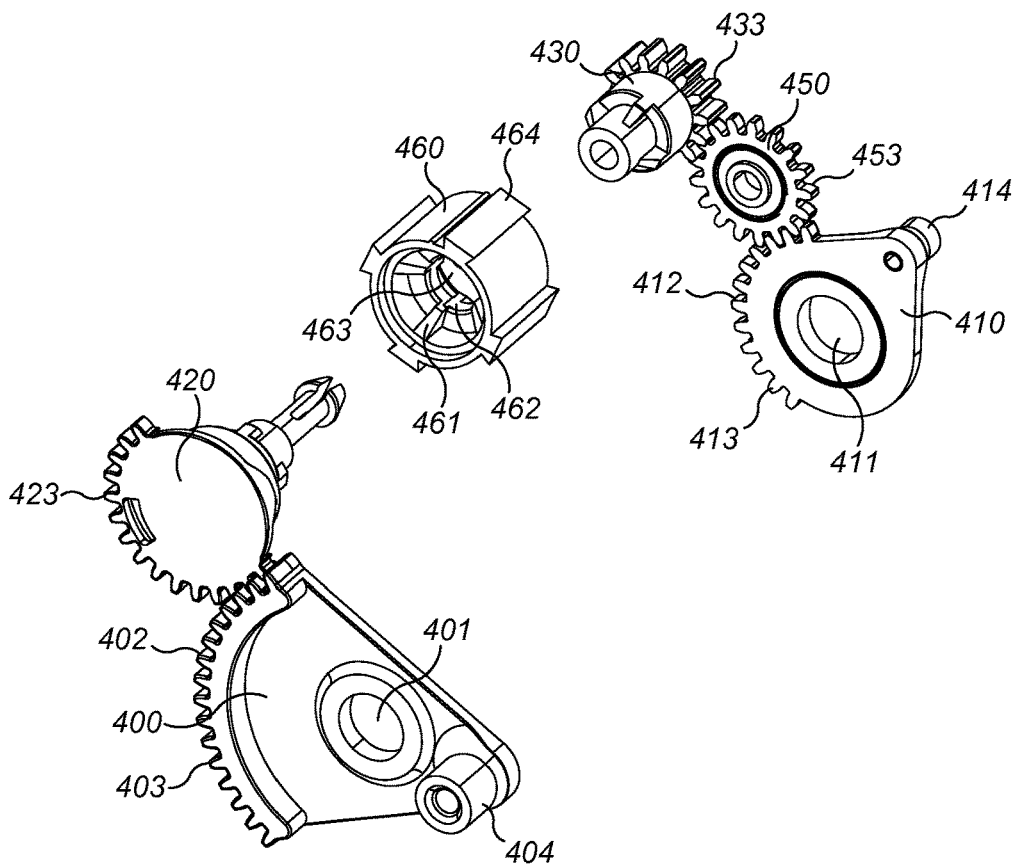
FIGS. 13A and 13B show expanded and assembled views of the indexing mechanism of the fourth embodiment.
Figure 13B:
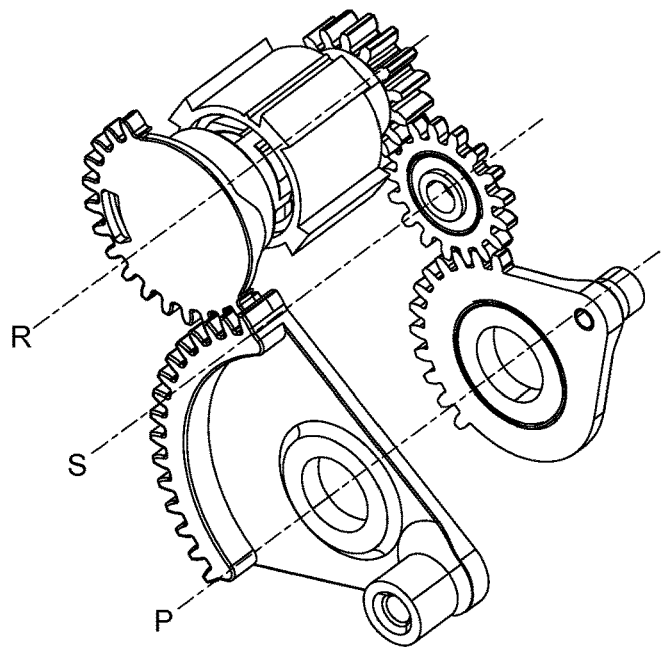

FIGS. 13A and 13B show expanded and assembled views of the indexing mechanism of the fourth embodiment. The mechanism is similar to that of the first embodiment, comprising a first (opening) actuator gear 400, a first drive gear 420, a blister strip indexing wheel 460, a second drive gear 430, an idler gear wheel 450 and a second (closing) actuator gear 410. However, unlike the first embodiment, there are no drive couplings.

The first and second actuator gears 400, 410 are formed as plate-like portions, each having a central pivot hole 401, 411 which fit onto the axles 7 (see FIG. 1) on either side of the housing, so that the actuator gears are mounted for rotation on the housing about the same axis P as the outer cover. The actuator gears 400, 410 each have gear elements 402, 412 which consist of teeth 403, 413 extending around part of the periphery of each gear.

The first and second actuator gears 400, 410 may be keyed or otherwise attached to the outer cover when the inhaler is assembled so that the first and second actuator gears and the outer cover rotate together. For example, round posts 404, 414 protrude from the actuator gears 400, 410 and are received in corresponding holes 15 in each side of the outer cover (see FIG. 1). Opening or closing the outer cover thereby causes the actuator gears 400, 410 to rotate about axis P. Alternatively, the first and second actuator gears 400, 410 and outer cover may be formed as a single component, for example they may be moulded together as a unitary piece.

The first and second drive gears 420, 430 and the indexing wheel 460 are mounted for rotation about axis R. The indexing wheel 460 comprises a number of spokes 461 (typically four) extending from a hub 462 which surrounds a central circular recess 463. The spokes are arranged so that a blister locates between the protruding ends 464 of successive spokes as the blister strip passes around the indexing wheel.

The first actuator gear element 402 transmits drive from the outer cover as it is rotated to the first drive gear 420 by means of the gear teeth 403 which mesh with corresponding gear teeth 423 on the first drive gear 420. The second actuator gear element 412 transmits drive from the outer cover as it is rotated via the idler gear wheel 450 to the second drive gear 430. The idler gear wheel is mounted for rotation on an idler gear axle 472 (shown in FIG. 15B) about axis S. The gear teeth 413 of the second actuator gear element mesh with corresponding gear teeth 453 on the idler gear wheel which in turn mesh with gear teeth 433 on the second drive gear 430.

Thus, as with the first embodiment, the first drive gear 420 rotates in response to rotation of the first actuator gear 400, and the second drive gear 430 rotates in response to rotation of the second actuator gear 410, but in the opposite sense, due to the presence of the idler gear wheel 450. The drive gears 420, 430 and rotate together with their respective actuator gear 400, 410 at all times. The difference over the first embodiment is the manner in which the drive gears 420, 430 selectively connect to and disconnect from the indexing wheel 460, in order to cause the indexing wheel 460 to rotate to index the blister strip.

Figure 14A:
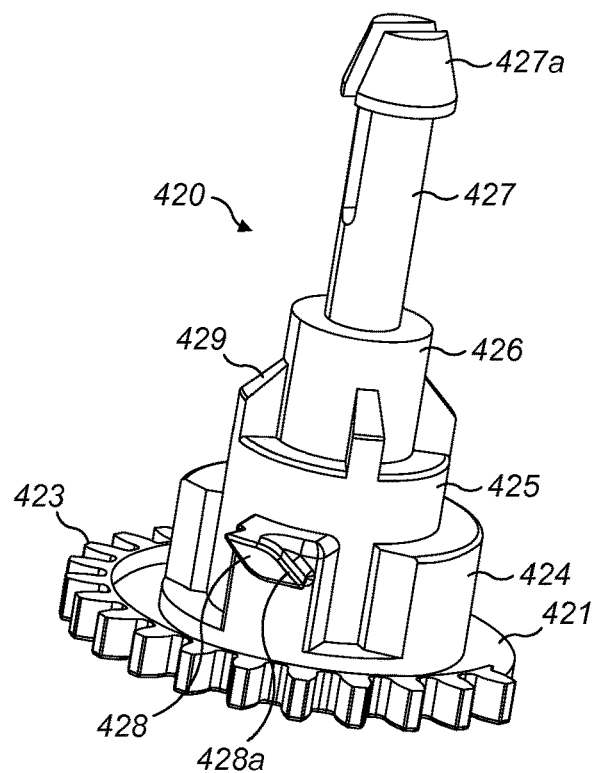
FIGS. 14A, 14B, 14C and 14D show perspective views from opposite sides of the first and second drive gears.
Figure 14B:
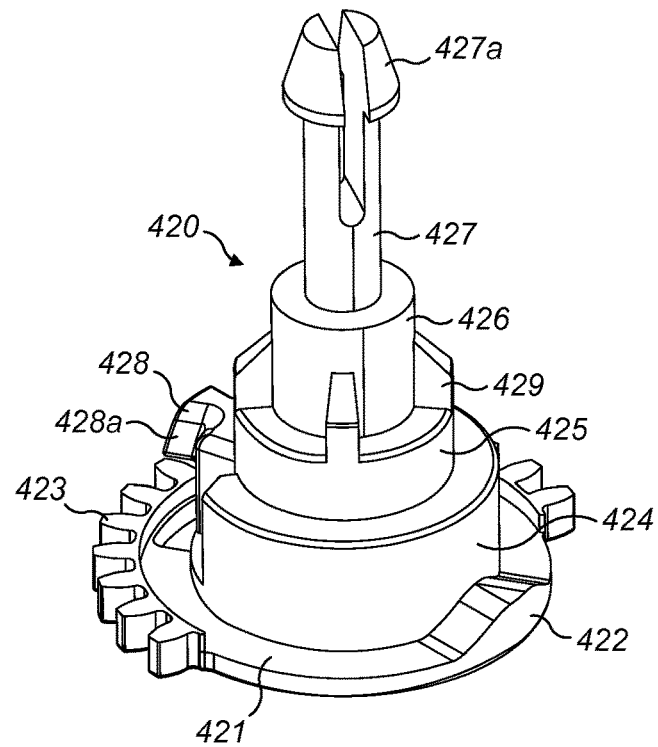
Figure 14C:
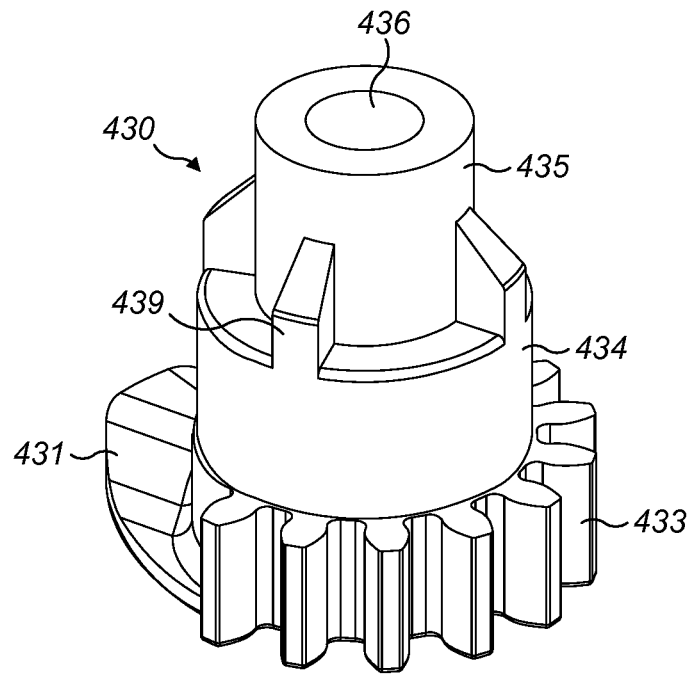
Figure 14D:
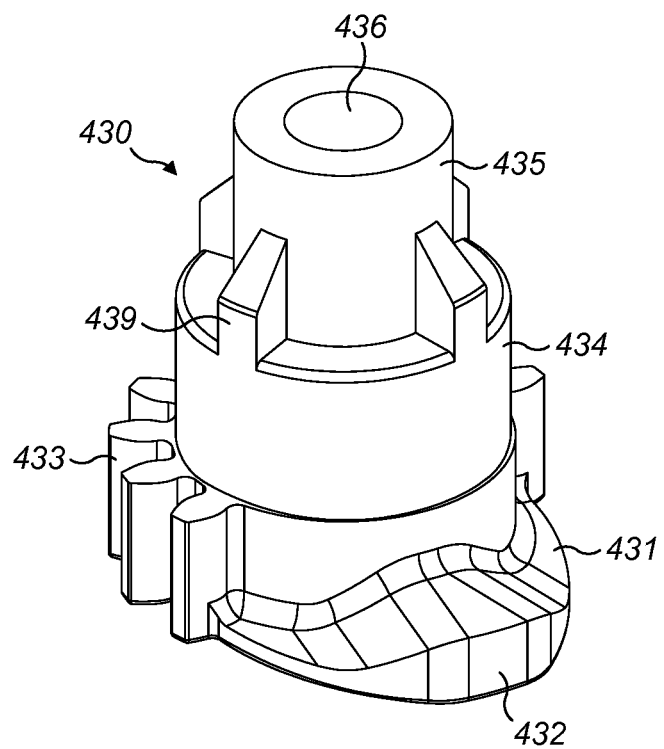
Figure 14E:
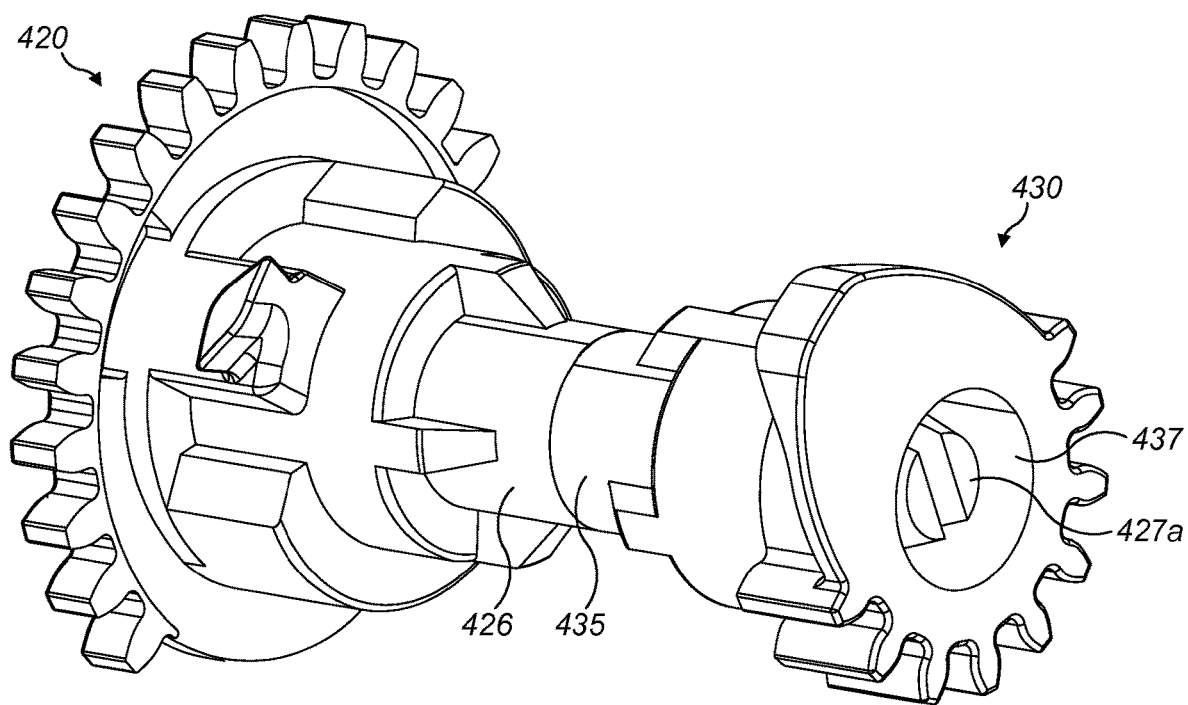
FIG. 14E shows a perspective view of the first and second drive gears connected together.

FIGS. 14A and 14B show perspective views from opposite sides of the first drive gear 420. FIGS. 14C and 14D show similar views of the second drive gear 430. FIG. 14E shows the first and second drive gears connected together, without the indexing wheel in order to show the features that would otherwise not be visible.

The first drive gear 420 comprises a flange 421 having a small hump on one side which functions as a first ramp follower 422, and a shaft which extends axially from the centre of the flange 421. Gear teeth 423 protrude radially from the flange around about half of its circumference on the side opposite the hump. The shaft has first, second, third and fourth cylindrical sections 424, 425, 426, 427 having different radii. The first shaft section 424, which has the largest radius, is adjacent to the flange. The fourth shaft section 427, which is furthest from the flange, has the smallest radius. The second 425 and third 426 shaft sections lie between the first 424 and fourth 427 shaft sections, and have intermediate radii. A track follower 428 protrudes radially from the first shaft section 424, diametrically opposite to the hump 422. The track follower 428 has first and second angled engaging faces 428a, 428b on its ends, so that it is rhomboid in shape (when viewed in the radial direction).

The second drive gear 430 comprises a flange 431 also having a hump which functions as a second ramp follower 432, and an axial shaft. Gear teeth 433 protrude radially from the shaft around about half of its circumference on the side opposite the flange 431 and hump 432. The shaft has first and second cylindrical sections 434, 435 with the same radii as the second 424 and third 425 shaft sections respectively of the first drive gear 420. A central circular hole 436 extends through the drive gear 430.

The fourth shaft section 427 of the first drive gear has a radius which corresponds to that of the central circular hole 436 of the second drive gear. A clip connection 427a is situated at the distal end of the fourth shaft section 427 and fits into a corresponding circular recess 437 on the outer side of the second drive gear 430, which is visible in FIG. 14E.

FIG. 14E shows the second drive gear 430 connected to and mounted for rotation on the fourth shaft section 427 of the first drive gear 420. The clip connection 427a and corresponding recess 437 hold the first 420 and second 430 drive gears together in the axial direction, whilst they are free to rotate independently of each other. The length of the fourth shaft section 427 (including the clip connection 427a) corresponds to the total thickness of the second drive gear 430. Thus, when the fourth shaft section 427 is inserted into the central circular hole 436, the third shaft section 426 of the first drive gear 420 abuts the second shaft section 435 of the second drive gear 430.

The radius of the third shaft section 426 of the first drive gear and of the second shaft section 435 of the second drive gear correspond to that of the central circular recess 463 of the indexing wheel 460. These shaft sections 426, 435 abut each other and together form a further bearing surface (visible in FIG. 14E) on which the indexing wheel 460 rotates, also on axis R.

Four equi-angularly spaced drive dogs 429, 439 protrude radially outwards from the third shaft section 426 of the first drive gear and from the second shaft section 435 of the second drive gear respectively. The drive dogs 429 on the first drive gear are formed as walls which extend axially from the second shaft section 425 along part of the third shaft section 426. Similarly, the drive dogs 439 on the second drive gear are formed as walls which extend axially from the first shaft section 434 along part of the second shaft section 435.

The drive dogs engage and disengage with the spokes of the indexing wheel in a manner which is described below. The axial faces of both the drive dogs and the spokes are sloped at an angle of 45°. This maximizes the contact area between the radial faces of the drive dogs and the spokes when they are engaged for the fixed axial engagement distance, which is limited by the distance that the drive gears translate as will be described below.

Figure 15A:
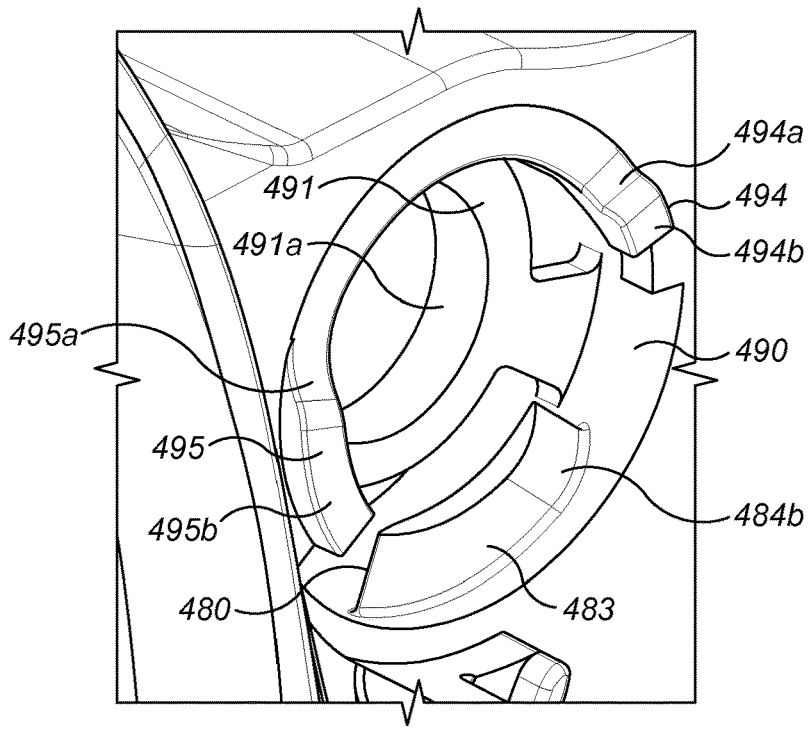
FIGS. 15A and 15B are perspective views of each side of the housing, showing the track formation and ramps.
Figure 15B:
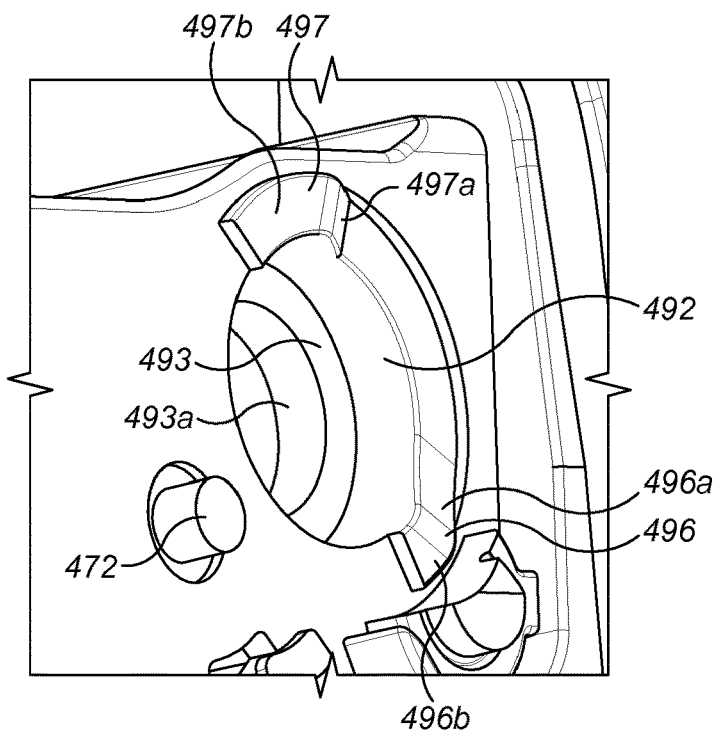
Figure 16A:
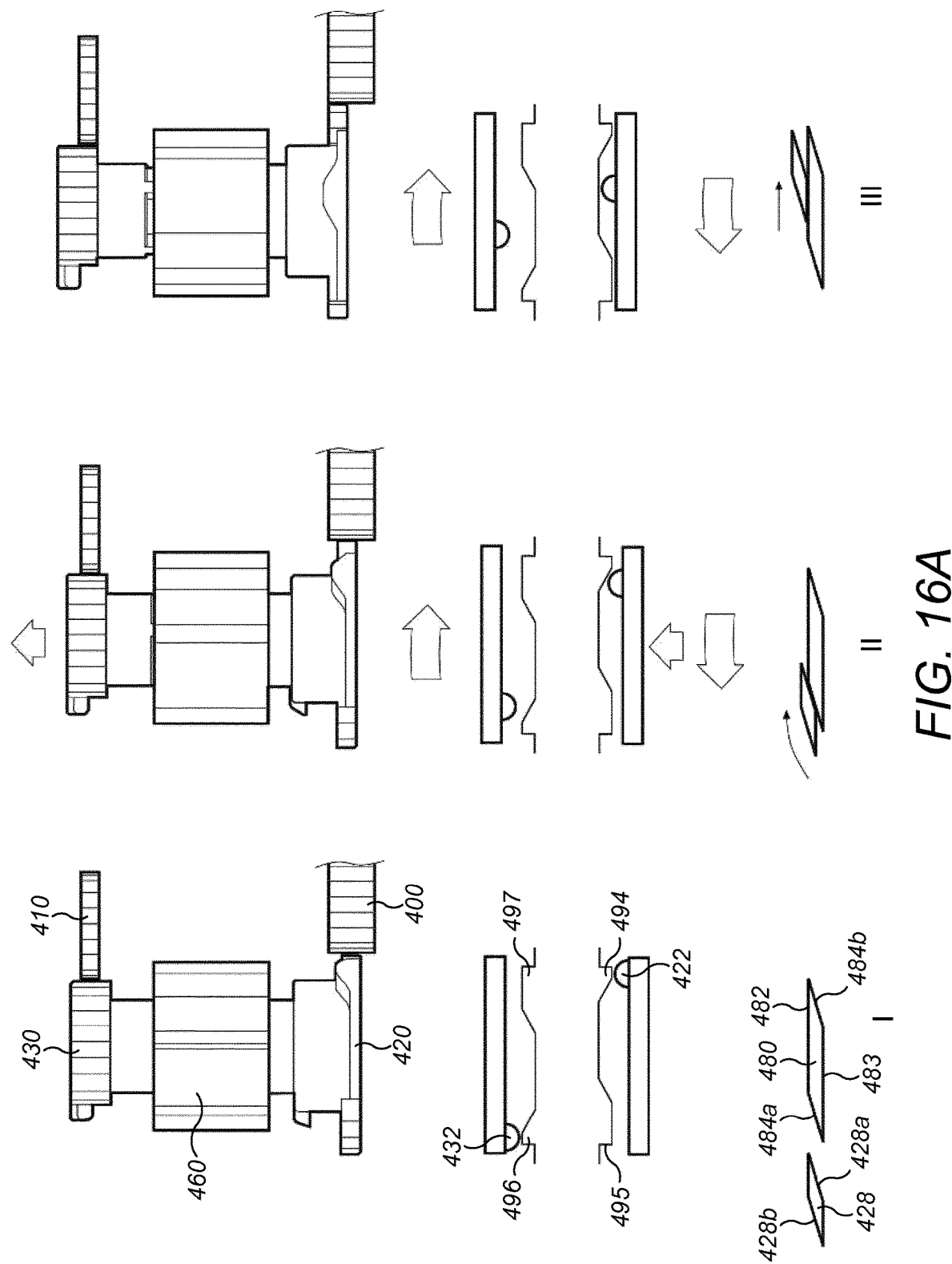
FIGS. 16A and 16B schematically shows the positions of the drive gears and the indexing wheel (top row), the ramps and ramp followers (middle row) and the track follower and the track formation (bottom row) at several stages during opening and closing of the outer cover.
Figure 16A:
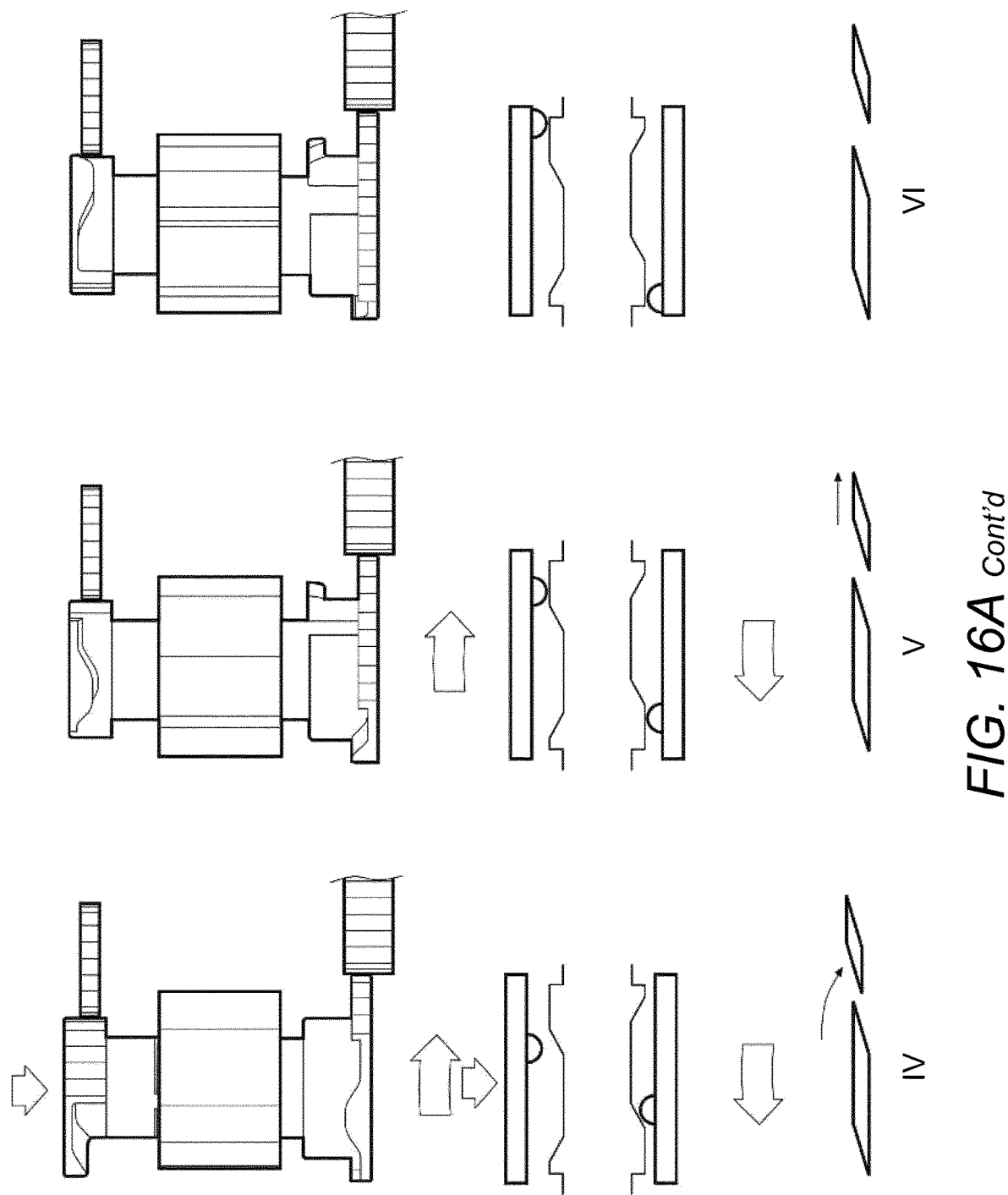
Figure 16B:
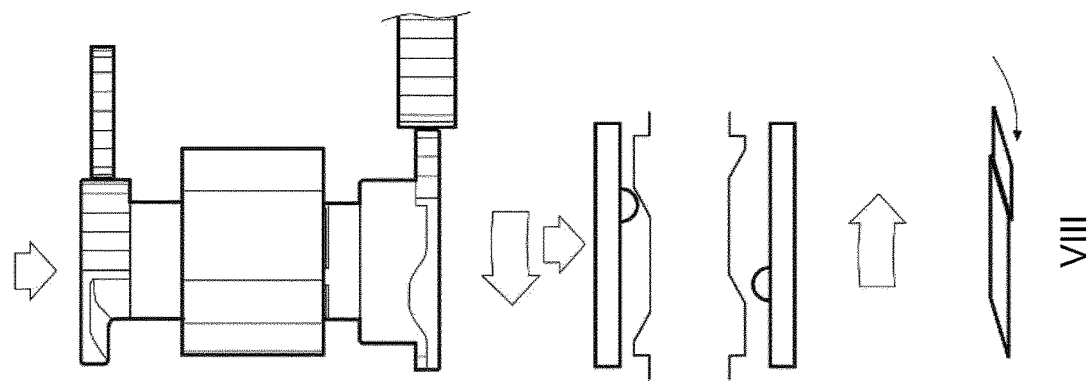
Figure 16B:
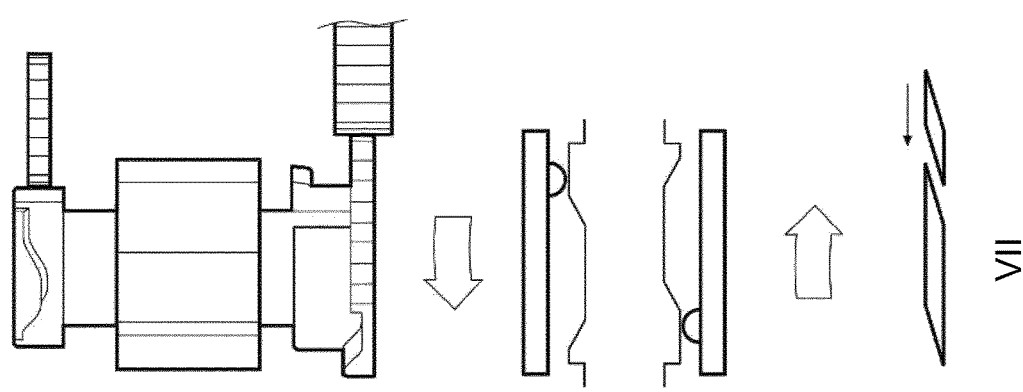
Figure 16B:
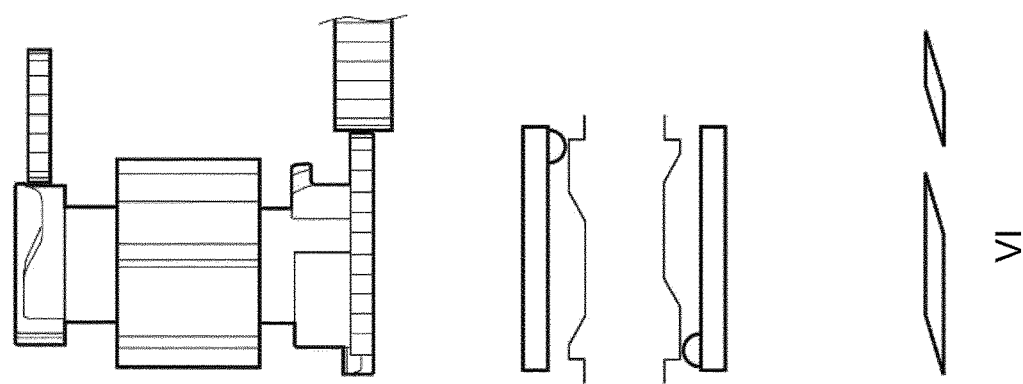
Figure 16B:
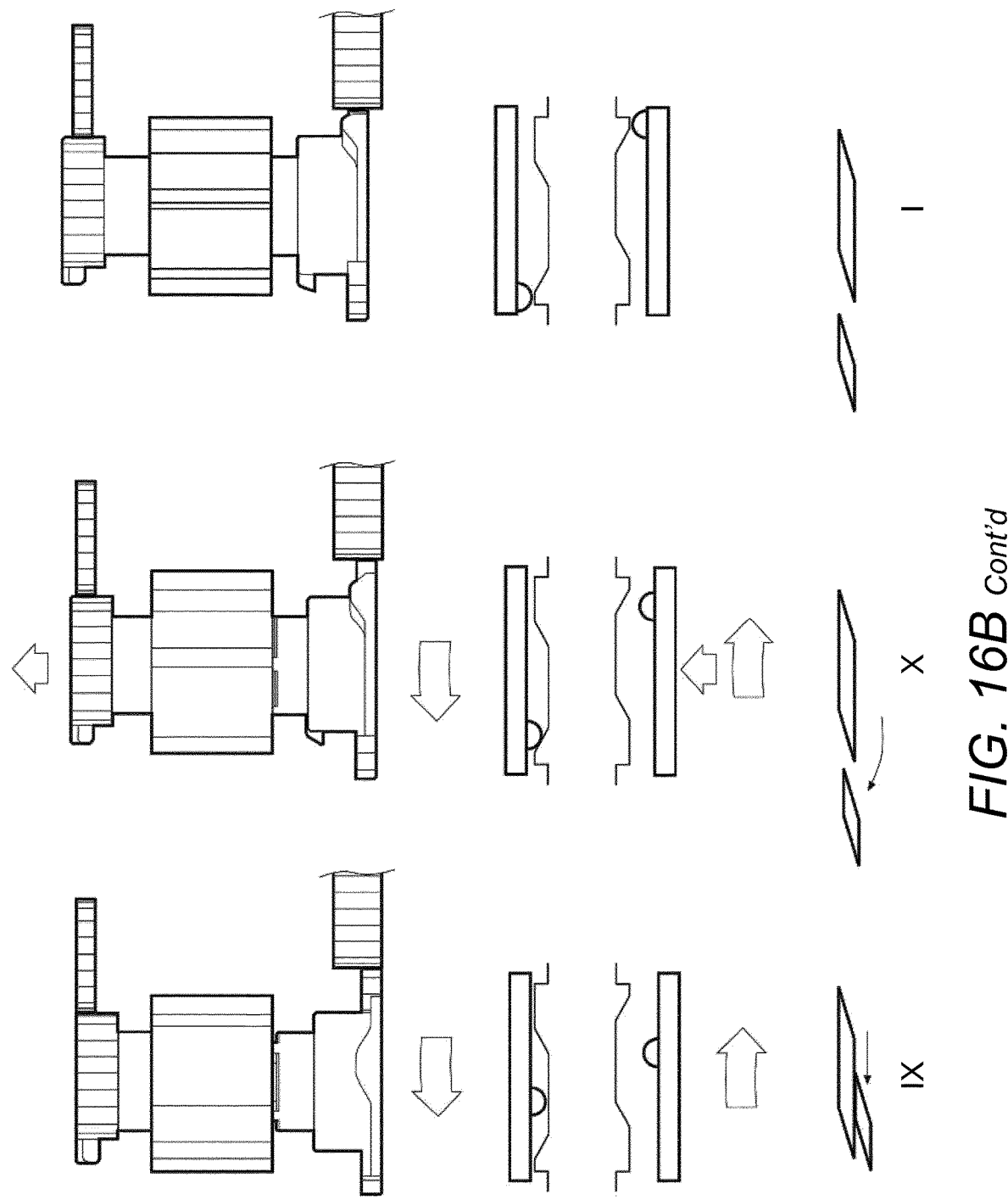

FIGS. 15A and 15B show close up views of the regions of the first (front) and second (rear) sides of the housing where the drive gears are located. The first side of the housing has a first circular recess 490 within which a first ring 491 is formed. Correspondingly, the second side of the housing has a second circular recess 492 a second ring 493. The radius of each ring 491, 493 corresponds to that of the second shaft section 425 of the first drive gear and the first shaft section 434 of the second drive gear.

The radially inward surface 491a of the first ring 491 thereby forms a bearing surface for the second shaft section 425 of the first drive gear which mounts the first drive gear for rotation about axis R. Similarly, the corresponding radially inward surface 493a of the second ring 493 forms a bearing surface for the first shaft section 434 of the second drive gear. The indexing wheel 460 is mounted for rotation about axis R on the bearing surface formed by the third shaft section 426 of the first drive gear 420 and the second shaft section 435 of the second drive gear 430. At the same time, it is held in place axially in the housing between the inner axial faces of the rings 491, 493 (these faces are not visible in FIGS. 15A and 15B).

As shown in FIG. 15A, a track formation 480 protrudes from the first circular recess 490, in the form of a barrier which separates and defines first and second tracks 482, 483 on either side, in the same way as the first embodiment. The ends of the barrier have angled faces 484a, 484b. Two ramps, a short close ramp 494 and a long pierce ramp 495, protrude from the outer side of the housing adjacent to and on opposite sides of the circular recess 490.

The second side of the housing, shown in FIG. 15B, has similar close and pierce ramps 496, 497 but does not have a track formation. The ramps correspond in size and shape to the ramps 494, 495 on the front side of the housing, but are located at different angular positions around the circular recess 492.

The track formation 480 on the first circular recess 490 and the track follower 428 on the first drive gear 420 operate in a similar manner to the first embodiment, but with some differences.

Firstly, unlike the first and second embodiments, there are no flexible portions that are deflected to cause engagement with the indexing wheel 460. Instead, the first and second drive gears themselves translate axially with respect to the indexing wheel 460 along axis R so that the drive dogs 429, 439 engage with the spokes 461 of the indexing wheel. The drive gears are able to translate axially because the second shaft section 425 of the first drive gear and the first shaft section 434 of the second drive gear can slide axially on the bearing surfaces 491*a*, 493*a*. The distance that the drive gears translate is equal to the width of the track formation 480 plus the width of the track follower 428. The absence of flexible parts has the advantage that the mechanism is robust and simple to manufacture.

Secondly, in order for the first and second drive gears to remain engaged with the first actuator gear and the idler gear respectively when they are translated, the teeth of one gear of each pair are thicker. As shown in FIGS. 13 and 14, the gear teeth 403, 433 of the first actuator gear 400 and the second drive gear 430 are thicker (axially) than the gear teeth 423, 453 of the first drive gear 420 and the idler gear 450 (however, the thicker and thinner teeth could equally be the other way around). In order to ensure that the gears are fully engaged in both drive positions, the thickness of the thicker gears is thickness of the thin gear plus the distance that the drive gears translate.

The third difference is the mechanism by which return to the neutral position is achieved. In contrast to the first embodiment, there is no flexible portion whose resilience causes it to spring back to its neutral (undeflected) position once the track follower has passed the central barrier. Instead, return to the neutral position is achieved by the ramps and ramp followers in the manner described below.

FIG. 16 shows the positions of the actuator gears 400, 410, the drive gears 420, 430 and the indexing wheel 460 (top row), the ramps 494, 495, 496, 497 and ramp followers 422, 432 and (middle row) and the track follower 428 and the track formation 480 (bottom row) at several stages during opening (FIG. 16A) and closing (FIG. 16B) of the outer cover. The track follower and ramp followers each move in a circular arc as the gears are rotated, but in FIG. 16, the motion is schematically shown as being linear for simplicity.

In stage I, the outer cover is in the closed position. The mechanism is in neutral, and the drive gears are located centrally with respect to the indexing wheel. Stages II, III and IV correspond to the first part of the opening stroke. The drive gears move axially relative to the indexing wheel in a manner that is described in detail below, so that the first drive gear engages with the spokes of the indexing wheel. Stage V is the second part of the opening stroke in which the first drive gear disengages from the indexing wheel and the mechanism is in neutral whilst the piercing elements are inserted. In stage VI, the outer cover is in the fully open position. Stage VII is the first part of the closing stroke in which the mechanism is in neutral whilst the piercing elements are removed. Stages VIII, IX and X correspond to the second part of the closing stroke. The drive gears move axially in the opposite direction, so that the second drive gear engages with the indexing wheel. Finally, at the end of the closing stroke, the drive gears return to the neutral central position and the cover is in the fully closed position of stage I.

The mechanism operates as follows. When the outer case is in the closed position (stage I), the drive dogs 429, 439 on both the first and second 420, 430 drive gears are spaced apart from the spokes 461 of the indexing wheel 460. The track follower 428 on the first drive gear 420 is spaced apart from the track formation 480. The ramp followers 422, 432 sit on the tops of their respective close (short) ramps 494, 496.

When the user opens the outer cover, the gears rotate. As indicated by the arrows in FIG. 16, the track follower 428 moves towards the track formation 480, so that the first angled engaging face 428*a* on the track follower comes into contact with the first angled engaging face 484*a* of the track formation 480. The track follower 428 rides up the angled engaging face 484*a* (stage II) to one side 482 of the track formation. This pushes the first drive gear 420 inwards towards the indexing wheel 460 as the ramp follower 422 on the first drive gear moves down the sloping section 494*a* of the first close ramp 494. The second drive gear (which is connected to the first drive gear by the clip connection 427*a*) correspondingly moves away from the indexing wheel and its ramp follower 432 moves clear of its close ramp 496. As the first drive gear moves inwards, the drive dogs 429 engage the spokes 461 of the indexing wheel 460. Consequently, as the track follower 428 moves along the first track 482 (stage III), the first drive gear 420 drives the indexing wheel 460 to rotate.

At the point when the track follower 428 reaches the end of the track formation 480 (stage IV), the ramp follower 422 on the first drive gear comes into contact with its long ramp 495. Further rotation of the outer cover, and hence the drive gears, causes the ramp follower 422 to ride up the angled section 495*a* of the pierce ramp 495. This pushes the first drive gear outwards so that the drive dogs 429 disengage from the spokes 461 of the indexing wheel, and pulls the second drive gear 430 inwards. The first ramp follower 422 reaches the flat section of the pierce ramp 495*b*, at which point the drive gears have returned to the central, neutral position. The ramp follower 432 on the second drive gear also comes into contact with the flat section 497*b* of the second pierce ramp 497 on the second (rear) side of the housing. This contact prevents the drive gears from overshooting the neutral position. This is the end of the first part of the opening stroke.

As with the first embodiment, the length of the track formation 480 controls the extent of rotation of the indexing wheel 460 relative to the extent of rotation of the drive gears 420, 430. Thus where two blisters are indexed and pierced on each actuation, the track length is chosen so that the indexing wheel is rotated through the correct angle to move the next, unused blister, into alignment with the blister piercing element during the opening stroke.

When the outer cover is rotated further during the second part of the opening stroke, drive to the indexing wheel is disengaged while the ramp followers 422, 432 move along the flat sections 495*b*, 497*b* of their respective pierce ramps until the outer cover reaches the fully open position. This second part of the stroke allows the blisters to be pierced while the indexing wheel is not being driven and the blister strip is stationary, in the same manner as before. In the fully open position (stage VI), the piercing elements have been inserted and the ramp followers 422, 432 are at the far ends of the flat sections of the pierce ramps 495*b*, 497*b*.

When the user closes the outer cover from the fully open position, the drive gears rotate back in the opposite directions. In the first part of the closing movement, the piercing elements are removed from the blisters and the ramp followers 422, 432 move back along the flat sections of the pierce ramps 495b, 497b while the drive gears remain in the central, neutral position (stage VII).

At the start of the second part of the closing movement, the second angled engaging face 428b of the track follower 428 contacts the second angled engaging face 484b of the track formation 480 (stage VIII) and the ramp followers 422, 432 reach the sloping sections 495a, 497a of the pierce ramps.

Further rotation of the outer cover, and hence the first drive gear causes the track follower 428 to ride along the angled engaging face 484b and move onto the second track 483. The first drive gear moves outwards and the second drive gear moves inwards towards the indexing wheel. The ramp follower 432 on the second drive gear moves down the sloping section 497a of the pierce ramp 497. The other ramp follower 422 moves clear of its pierce ramp 495. As the second drive gear moves inwards, its drive dogs 439 engage the spokes 461 of the indexing wheel 460.

The indexing wheel 460 is now driven by the second drive gear 430 while the track follower moves along the second track 483 (stage IX). Since the second drive gear rotates in the opposite sense to the first drive gear due to the idler gear, the blister strip is indexed forwards (not backwards) by the closing of the outer cover, as in the first embodiment.

At the point when the track follower reaches the end of the track formation 480 (stage X), the ramp follower 432 on the second drive gear comes into contact with the close ramp 496 on the second (rear) side of the housing. Further rotation of the outer cover, and hence the drive gears causes the ramp follower 432 to ride up the angled section 496a of the ramp 496. This pulls the second drive gear outwards so that the drive dogs 439 disengage from the spokes 461 of the indexing wheel, and pulls the first drive gear 430 inwards.

The second ramp follower 432 reaches the top of the close ramp 496b, at which point the drive gears have returned to the central, neutral position. The ramp follower 422 on the first drive gear also comes into contact with the top 494b of the first close ramp 494. This contact prevents the drive gears from overshooting the neutral position. This is the end of the closing stroke, and the mechanism has returned to its initial, fully closed position (stage I).

Thus the linked drive gears act as a shuttle, which is driven axially by the track formation, the track follower, the ramps and the ramp followers. The motion of the shuttle changes the gearing between the outer cover and the indexing wheel from drive during the first part of the opening stroke, into neutral during the second part of the opening stroke and the first part of the closing stroke, and then into drive during the second part of closing. Consequently the blister strip is indexed forwards during both opening and closing.

Although the indexing mechanisms are different, the four embodiments described above have a number of common features and advantages.

Firstly, all of the mechanisms are in a stable, neutral configuration when the outer cover is in the closed position. None of the components is under stress in this position; furthermore, if an external force is applied to the device, for example by dropping it, the mechanism remains in neutral and cannot be accidentally forced into a drive position.

Secondly, actuation of the inhaler is reversible during the first part of the opening stroke, up to the point at which the flange deflecting dog/track follower passes the end of the track formation/central barrier. The user can abort actuation simply by closing the outer cover, which moves the blister strip back to its previous position. Moreover, the closing stroke is reversible through both the first part when the piercing elements are removed and through most of the second part during which the blister strip is indexed, i.e. up to the point at which the flange deflecting dog/track follower passes the other end of the track formation/central barrier. Thus, for example, if the user accidentally begins to close the outer case without having inhaled, they can simply open it again, inhale and then close as normal.

Thirdly, each of the embodiments can straightforwardly be re-configured into a conventional inhaler that delivers the contents of one blister on each actuation, either by modifying the blister strip or by omitting some components of the device. Thus, by using a strip in which each blister is each half-filled, or with alternating full and empty blisters, a single dose is dispensed when two blisters are indexed and pierced on each actuation. Alternatively, omitting the second piercing element, second actuator gear, second drive gear and idler wheel provides an inhaler which indexes on opening only and pierces one blister on each actuation. Thus, a single overall design with one set of components can provide both conventional, and double indexing inhalers Instead of causing indexing and piercing, the outer cover could alternatively be passive, so that opening or closing it exposes or covers the mouthpiece, but does not actuate the device. In this case, the inhaler includes a separate actuating lever which is revealed when the outer cover is rotated out of its closed position. The lever may have a protruding button to facilitate actuation by the user, as described in, for example, WO 13/175176. The actuating lever is connected to the actuator gears in an analogous manner to the outer cover in the embodiments described above. Thus in this variant of the first and fourth embodiments, in which the drive gears selectively engage and disengage with the indexing wheel, the actuating lever (instead of the outer cover) is keyed or otherwise attached to the outer cover, and indeed may be formed (e.g. moulded) as a single component with the first and second actuator gears. In this variant of the second and third embodiments, the actuating lever (instead of the outer cover) is connected to the drive coupling, so that rotation of the actuating lever causes rotation of the drive coupling. The outer cover and actuator may also include cooperating means configured so that, after inhalation, when the user rotates the outer cover back into its closed position in which it covers the mouthpiece, the actuator is also rotated back into its initial position. In other words, the outer cover is passive during opening, but is linked to the actuator during closing.

Instead of the indexing mechanism being disengaged before piercing, the indexing mechanism could be configured so that the indexing mechanism is disengaged after the blister piercer has begun to pierce the lid of a blister so that each piercing element is drawn across and through the lid of the blister as it enters it. This creates larger openings than those created when the strip is stationary during piercing, which can help to ensure that the drug dose is entrained in the airflow and removed from the blister.

Other opening means may be used instead of a piercer; for example the blisters may be opened by peeling the lid from the base, or by folding the blister so that the lid is burst open, as described in WO 16/083102.

In addition to the airflow through the blisters, the inhaler may also have one or more bypass airflow channels. Air flows through the bypass channel from outside the device and into the mouthpiece, without passing through the blister. The bypass airflow reduces the resistance of the device. The size of the bypass is chosen so that sufficient air nonetheless flows through the blisters to ensure complete evacuation of the powder.

Preferably the inhaler retains the used blisters. More preferably the inhaler has a wall to separate the interior of the housing into used and unused blister compartments. The wall is preferably rigid and slideably mounted so that the sizes of the unused and used blister compartments change relative to each other as the number of blisters that are used increases and the number of unused blisters decreases.

The used blisters are preferably crushed so that they take up less space. Thus the blister strip indexing wheel is preferably positioned such that the distance between the hub and the inner surface of the housing is less than the depth of a blister so that onward rotation of the wheel after piercing causes a blister to be at least partially squashed between the hub and the wall.

The inhaler may be either passive or active. In a passive inhaler, the dose is entrained in a flow of air caused when the user inhales through the mouthpiece. An active inhaler includes means for generating a pressurized flow of gas or air through the blister to entrain the dose and carry it out of the blister through the mouthpiece and into the user's airway. Although the term "mouthpiece" is used, the invention is also applicable to devices in which the dose is inhaled through the nasal passages.

The invention claimed is:

1. An inhaler comprising:
   a housing which contains a blister strip having a plurality of blisters which contain powdered medicament for inhalation,
   a mouthpiece mounted to the housing through which the medicament is inhaled by a user,
   an indexing wheel for indexing the blister strip and an opening mechanism for opening the blisters,
   wherein the blister strip is indexed by forward motion of an actuator from a first position to a second position, characterized in that the blister strip is also indexed in the same direction by reverse motion of the actuator from the second position to the first position,
   wherein the indexing wheel is arranged to index the blister strip forward by a distance between a center of a first blister and a center of a successive blister on the blister strip on the forward motion of the actuator and to index the blister strip forward the same distance on the reverse motion of the actuator,
   and wherein the opening mechanism is arranged to open two successive blisters on one complete actuation of the actuator.

2. An inhaler according to claim 1, wherein the inhaler has an outer cover which is pivotally mounted on the housing.

3. An inhaler according to claim 2, wherein the outer cover forms the actuator, wherein in the first position the outer cover is closed so that the mouthpiece is covered, and in the second position the outer cover is open so that the mouthpiece is exposed, and so that motion of the outer cover causes indexing of the blister strip and opening of the blisters.

4. An inhaler according to claim 1, wherein the inhaler has a lever which forms the actuator so that motion of the lever causes indexing of the blister strip and opening of the blisters.

5. An inhaler according to claim 1, wherein the opening mechanism comprises a piercer and the indexing wheel indexes the two successive blisters into alignment with the piercer for piercing.

6. An inhaler according to claim 5, wherein the blister strip is indexed during a first part of the forward motion of the actuator, the piercer pierces the two successive blisters during a second part of the forward motion, the piercer is removed during a first part of the reverse motion of the actuator and the blister strip is indexed again during a second part of the reverse motion.

7. An inhaler according to claim 1, wherein the inhaler further comprises first and second drive gears, and an idler gear, wherein the actuator is drivingly linked to the first drive gear, and to the second drive gear via the idler gear so that the first and second drive gears rotate in opposite senses during motion of the actuator; wherein the first drive gear drives the indexing wheel during at least part of the forward motion of the actuator, and does not drive the indexing wheel during the reverse motion of the actuator; and the second drive gear drives the indexing wheel during at least part of the reverse motion of the actuator, and does not drive the indexing wheel during the forward motion of the actuator.

8. An inhaler according to claim 7, wherein the inhaler further comprises first and second actuator gears which are connected to and driven by the actuator, wherein the first actuator gear drives the first drive gear, and the second actuator gear drives the idler gear which in turn drives the second drive gear.

9. An inhaler according to claim 7, wherein the first and second drive gears are axially linked together to form a shuttle whilst being free to rotate independently, wherein the first and/or second drive gear has a track follower which interacts with a track formation on the housing to cause the shuttle to translate axially relative to the indexing wheel so that the first and second drive gears engage and disengage with the indexing wheel.

10. An inhaler according to claim 9, wherein the first and second drive gears each have a ramp follower which interacts with ramps on the housing to cause the first and second drive gears to disengage with the indexing wheel when the actuator is in the first or second position.

11. An inhaler according to claim 7, wherein a first drive coupling is connected to the first drive gear, a second drive coupling is connected to the second drive gear, and the drive couplings engage and disengage with the indexing wheel.

12. An inhaler according to claim 1, wherein the inhaler further comprises first and second drive gears that are connected to the indexing wheel, and an idler gear, wherein the actuator is drivingly linked to the first drive gear during at least part of the forward motion of the actuator, and is not drivingly linked to the first drive gear during the reverse motion of the actuator; and the actuator is drivingly linked to the idler gear and the second drive gear during at least part of the reverse motion of the actuator, and is not drivingly linked to the second drive gear during the forward motion of the actuator.

13. An inhaler according to claim 12, wherein a dual drive coupling is connected to and driven by the actuator, and the dual drive coupling goes into and out of driving linkage with the first and second drive gears.

14. An inhaler according to claim 13, wherein the inhaler further comprises a first actuator gear which drives the first drive gear and a second actuator gear which drives the idler gear which in turn drives the second drive gear, so that the first and second actuator gears rotate in opposite senses during motion of the actuator, and wherein the dual drive coupling engages and disengages with the first and second actuator gears.

15. An inhaler according to claim 1, wherein the two blisters contain different medicaments.

* * * * *